United States Patent
Weiss

(10) Patent No.: US 12,312,390 B2
(45) Date of Patent: *May 27, 2025

(54) RAPID-ACTING INSULIN ANALOGUES OF ENHANCED STABILITY

(71) Applicant: CASE WESTERN RESERVE UNIVERSITY, Cleveland, OH (US)

(72) Inventor: Michael A. Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 558 days.

This patent is subject to a terminal disclaimer.

(21) Appl. No.: 17/562,435

(22) Filed: Dec. 27, 2021

(65) Prior Publication Data

US 2022/0112262 A1   Apr. 14, 2022

Related U.S. Application Data

(63) Continuation of application No. 16/462,440, filed as application No. PCT/US2017/062772 on Nov. 21, 2017, now Pat. No. 11,208,453.

(60) Provisional application No. 62/424,892, filed on Nov. 21, 2016.

(51) Int. Cl.
*C07K 14/62* (2006.01)
*A61P 3/10* (2006.01)
*A61K 38/00* (2006.01)

(52) U.S. Cl.
CPC ........... *C07K 14/62* (2013.01); *A61P 3/10* (2018.01); *A61K 38/00* (2013.01)

(58) Field of Classification Search
CPC ............ C07K 14/7151; A61K 38/00; A61K 2039/505
See application file for complete search history.

(56) References Cited

U.S. PATENT DOCUMENTS

| 9,260,502 B2 | 2/2016 | Nielsen et al. |
| 10,561,711 B2 | 2/2020 | Joseph |
| 2011/0098440 A1* | 4/2011 | Madsen ............ C07K 14/62 530/303 |
| 2011/0195896 A1 | 8/2011 | Weiss et al. |
| 2014/0128319 A1 | 5/2014 | Weiss |

FOREIGN PATENT DOCUMENTS

WO     2016118631 A1   7/2016

* cited by examiner

*Primary Examiner* — Gyan Chandra
(74) *Attorney, Agent, or Firm* — Hahn Loeser & Parks, LLP; John J. Cunniff

(57) ABSTRACT

A two-chain insulin analogue contains a modified A-chain polypeptide and a modified B-chain polypeptide. The A-chain polypeptide comprises one or more of: a His or Glu substitution at position A8, a Glu substitution at position A14; and a Gln or Arg substitution at position A17. The B-chain polypeptide comprises one or more of: a deletion of the amino acids at position B1, B1-B2, B1-B3, B30 or a combination thereof; an Ala or Glu substitution at position B2; a Glu substitution at position B3. The analogue exhibits thermodynamic stability in a zinc-free solution, decreased self-association, maintains biological potency, and no increased mitogenicity. The analogue exhibits resistance to chemical degradation and physical degradation. A method of treating a patient with diabetes mellitus or obesity comprises administering a physiologically effective amount of the insulin analogue or a physiologically acceptable salt thereof to a patient.

10 Claims, 10 Drawing Sheets
Specification includes a Sequence Listing.

PROINSULIN

MODEL

RAPID-ACTING INSULIN ANALOGUES OF ENHANCED STABILITY

CROSS REFERENCE TO RELATED APPLICATIONS

This application is a continuation of co-pending U.S. application Ser. No. 16/462,440, filed May 20, 2019, which is a national stage application of International Application number PCT/US2017/062772, having a filing date of Nov. 21, 2017, and claiming benefit of U.S. Provisional Application No. 62/424,892 filed on Nov. 21, 2016.

STATEMENT REGARDING FEDERALLY SPONSORED RESEARCH OR DEVELOPMENT

This invention was made with government support under grant numbers DK040949 and DK074176 awarded by the National Institutes of Health. The government has certain rights in the invention.

BACKGROUND OF THE INVENTION

This invention relates to polypeptide hormone analogues that exhibit enhanced pharmaceutical properties, such as increased thermodynamic stability, decreased mitogenicity, and feasibility of a rapid-acting formulation at high protein concentrations (1-5 mM) in the absence of zinc ions. More particularly, this invention relates to insulin analogues that confer rapid action at increased formulation strengths (relative to wild-type insulin) and/or that enable use of a broader range of excipients in a pharmaceutical formation (relative to wild-type insulin or conventional insulin analogues as traditionally formulated as zinc-ion-stabilized protein assemblies).

The engineering of non-standard proteins, including therapeutic agents and vaccines, may have broad medical and societal benefits. Naturally occurring proteins—as encoded in the genomes of human beings, other mammals, vertebrate organisms, invertebrate organisms, or eukaryotic cells in general—may have evolved to function optimally within a cellular context but may be suboptimal for therapeutic applications. Analogues of such proteins may exhibit improved biophysical, biochemical, or biological properties. A benefit of protein analogues would be to achieve enhanced "on-target" activity (such as metabolic regulation of metabolism leading to reduction in blood-glucose concentration) with decreased unintended and unfavorable side effects, such as promotion of the growth of cancer cells. Another benefit of such protein engineering would be preservation of rapid onset of action on concentration of the protein to achieve formulations of higher strength. Yet another example of a societal benefit would be enhanced compatibility with a delivery device, such as an insulin pump or a closed-loop system in which an algorithm connects the flow rate of the pump to the output of a continuous glucose monitor. An example of a therapeutic protein is provided by insulin. Wild-type human insulin and insulin molecules encoded in the genomes of other mammals bind to insulin receptors is multiple organs and diverse types of cells, irrespective of the receptor isoform generated by alternative modes of RNA splicing or by alternative patterns of post-translational glycosylation. Wild-type insulin also binds with lower but significant affinity to the homologous Type 1 insulin-like growth factor receptor (IGF-1R).

Insulin is a two-chain protein molecule that in a vertebrate animal is the biosynthetic product of a single-chain precursor, designated proinsulin. The sequence and structure of human proinsulin are illustrated in FIGS. 1A (SEQ ID NO: 1) and 1B, respectively; the sequence of human insulin is shown in FIG. 1C. Insulin contains two polypeptide chains, an A chain, containing 21 residues (SEQ ID NO: 2), and a B chain containing 30 residues (SEQ ID NO: 3). Specific amino acids in one or the other chain are designated below by the standard three-letter code (for example, "Ala" for Alanine or "Asp" for Aspartic Acid) followed by a letter, optionally in superscript, that designates the chain (A or B) and position number in that chain relative to wild type insulin. For example, Histidine at position 10 of the B chain is designated $His^{B10}$, Valine at position 12 of the B chain is designated $Val^{B12}$, and Threonine at position 8 of the A chain is designated $Thr^{A8}$. Alternatively, amino acids may be designated by the standard one-letter code (for example, "A" for Alanine or "D" for Aspartic Acid) followed by a letter designating the A or B chain, followed by position number relative to wild type insulin. Under this convention, Histidine at position 10 of the B chain is designated HB10, Valine at position 12 of the B chain is designated VB12, and Threonine at position 8 of the A chain is designated TAB. The numbering of the amino acids is maintained relative to wild type insulin, even in the presence of deletions of amino acids from the N-terminal end of a polypeptide. Therefore, in a des B1 insulin analogue, which indicates that the first amino acid has been deleted from the N-terminal end of the wild type sequence, the first amino acid of the B-chain is Valine, which is still designated as occupying the B2 position. Likewise, in a des [B1, B2] insulin analogue, in which the first two N-terminal amino acids have been deleted from a wild type sequence, the first amino acid is Asparagine, which is still designated as occupying the B3 position.

The term "insulin analogues" designates a class of molecules related to wild-type insulin by substitution of one more amino-acid residues by a different type of amino acid or by modifications of one or more atoms in the side chain or main chain of such residues by a different atom or set of atoms, but will still maintain at least a portion of one or more properties of wild-type insulin, such as the ability to bind insulin receptor (IR). An example of an insulin analogue known in the art is insulin lispro, in which $Pro^{B28}$ is substituted by Lys and $Lys^{B29}$ is substituted by Pro. Insulin lispro (also designated KP-insulin) is the active component of the product Humalog® (Eli Lilly and Co.).

It is known in the art that the B chain of insulin may be modified through amino-acid substitutions at one or a few positions to enhance the rate of absorption of an insulin analogue formulation from the subcutaneous depot. Insulin formulations of increased strength (international units per ml) promise to be of particular benefit for patients who exhibit marked insulin resistance and may also be of value in internal or external insulin pumps, either to extend the reservoir life or to permit miniaturization of the reservoir in a new generation of pump technologies.

Existing insulin products typically exhibit prolonged pharmacokinetic and pharmacodynamics properties on increasing the concentration of the insulin or insulin analogue to achieve formulation strengths greater than or equal to U-200 (200 international units/ml). Such prolongation impairs the efficacy of such products for the prandial control of glycemia on subcutaneous injection and impairs the efficacy and safety of pump-based continuous subcutaneous infusion. In light of these disadvantages, the therapeutic and societal benefits of rapid-acting insulin analogue formulations would be enhanced by the engineering of insulin analogues that retain rapid action at strengths between U-200 and U-1000 (inclusive of these lower and upper bounds). Additional benefits would accrue if the novel soluble insulin analogue exhibited weaker affinity for the Type 1 IGF receptor relative to wild-type human insulin. Still additional therapeutic and societal benefit would accrue if the concentrated insulin analogue formulation should exhibit reduced mitogenicity in assays developed to monitor insulin-stimulated proliferation of human cancer cell lines and/or in assays developed to monitor insulin-directed changes in gene expression associated with the stimulation or arrest of cellular proliferation.

Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinopathy, blindness, and renal failure.

Insulin is a small globular protein that plays a central role in metabolism in vertebrates. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain. A variety of evidence indicates that it consists of an insulin-like core and disordered connecting peptide. Formation of three specific disulfide bridges (A6-A11, A7-B7, and A20-B19) is coupled to oxidative folding of proinsulin in the rough endoplasmic reticulum (ER). Proinsulin is converted to insulin in the trans-Golgi network en route to storage as zinc insulin hexamers in the glucose-regulated secretory granules within pancreatic beta-cells.

FIG. 2 is a schematic representation of the pharmacokinetic principles underlying the design of prandial (rapid-acting) insulin analogs as known in the art. Whereas in a subcutaneous depot the insulin hexamer (upper left) is too large to efficiently penetrate into capillaries (bottom), more rapid uptake is mediated by the insulin dimer (center top) and insulin monomer (upper right). Prandial insulin products Humalog® and Novolog® contain insulin analogues (insulin lispro and aspart, respectively) with amino-acid substitutions at or near the dimerization surface of the zinc insulin hexamer such that its rate of disassembly is accelerated; prandial insulin product Apidra® (insulin deglulisine) is formulated as zinc-free oligomers (as a coupled equlibria) that likewise exhibit rapid rates of diassassembly in the depot. The insulin analogues of the present invention provide isolated insulin monomers and weakly associating dimers whose augmented stability enables formulation in the absence of zinc-mediated assembly or zinc-free higher-order assembly. The hexamer at upper left depicts a $T_3R^f_3$ zinc hexamer in which the A chain is shown in light gray, and B chain in dark gray; three bound phenolic ligands are shown as CPK models (paired ovals). The dimer at center depicts a zinc-free T2 dimer in which the A chain is shown in dark gray, and B chain in light (residues B1-B23 and B29-B30) or medium gray (B24-B28; anti-parallel beta-sheet); dimer-related inter-chain hydrogen bonds are shown in dotted line. A collection of crystallographic protomers (T, R and $R^f$) is shown at upper right wherein the A chain is shown in dark gray, and B chain in medium gray (B1-B9) and light gray (B10-B30).

Rapid action of insulin analogue formulations following their subcutaneous injection may reflect the pharmacokinetic properties of protein absorption from the subcutaneous depot and/or the pharmacodynamics properties of the insulin analogue once the insulin receptor is engaged within target tissues Amino-acid substitutions within insulin analogue formulations of the present invention may employ one or both of these mechanisms.

Substitutions at positions B28 and/or B29 are known in the art to impair the strength of zinc-free insulin dimerization and the stability of the zinc insulin analogue hexamer. However, substitution of the wild-type residues $Pro^{B28}$-$Lys^{B29}$ by $Lys^{B28}$-$Pro^{B29}$ (insulin lispro, the active component of Humalog® in a zinc-stabilized formulation) and substitution of $Pro^{B28}$ by Asp (insulin aspart, the active component of Novolog® in a zinc-stabilized formulation) impair the thermodynamic stability, chemical stability and physical stability of insulin, demonstrating that in general amino-acid substitutions in insulin confer a tradeoff between favorable and unfavorable properties. Substitution of $Lys^{B29}$ by Glu (one of two substitutions in insulin glulisine, the active component of Apidra®) with retention of wild-type $Pro^{B28}$ has a more limited effect on dimerization or hexamer stability, but permits stable formulation in a zinc-free solution at neutral pH. Despite potential pharmacodynamics advantages of a foreshortened tail of insulin action, such substitutions may incur tradeoffs in protein design as the introduced amino-acid residues impair the stability or receptor-binding affinity of insulin to an extent that is difficult to predict.

There are medical and societal needs for a rapid-acting insulin analogue or even an ultra-rapid-acting insulin analogue in a soluble formulation at neutral pH at strengths in the range U-200 through U-1000 (inclusive of these lower and upper values). A barrier to such products has long been posed by the complex self-association properties of wild-type insulin, which at neutral pH can form a concentration-dependent distribution of monomeric, dimeric, trimeric, tetrameric, hexameric, dodecameric, and higher-order species. Traditional insulin formulations known in the art typically employ a predominance of zinc insulin hexamers at a nominal protein concentration, in monomer units, of 0.6 mM (lower on dilution), whose native self-assembly and stabilized by the zinc ions and protects the hormone from physical and chemical degradation. Concentrating wild-type insulin hexamers above this protein concentration leads to progressive hexamer-hexamer interactions; this further level of self-association is associated with delayed absorption of the injected insulin from a subcutaneous depot, leading in turn to prolonged pharmacokinetics and pharmacodynamics. Analogous prolongation of current prandial insulin analogue products (Humalog®, Novolog® and Apidra®) occurs on their concentration above ca. 2 mM (in monomer units).

To overcome this barrier, we envisaged a novel route toward the engineering of rapid-acting insulin analogue formulations with increased strength. The first approach was to design ultra-stable insulin monomers whose dimerization and higher-order self-assembly at protein concentrations as high as 3-8 mM would not impose kinetic barriers to protein disassembly in the subcutaneous depot. In this approach the augmented intrinsic stability of the individual insulin analogue molecules would render its zinc-mediated hexamer assembly unnecessary for a stable formulation, i.e., in accordance with guidelines of the U.S. Food & Drug Administration with respect to chemical degradation, polymerization and fibrillation. In the absence of zinc coordination, the time scale of insulin self-assembly and disassembly is markedly more rapid than in the presence of zinc coordination; the difference is further magnified by the combination of zinc ions and preservatives typically employed in standard pharmaceutical formulations as this combination of excipients, which yields an "$R_6$" type hexamer that is exceptionally long-lived in the conformational equilibrium formed in such a formulation. It is a feature of the present invention that such analogues retain at least 20% of the biological activity of wild-type insulin on a per-molecule basis.

An insulin analogue known in the art to exhibit enhanced intrinsic stability in the absence of zinc ions and decreased self-assembly beyond the dimer is provided by $Asp^{B10}$-insulin. The wild-type residue ($His^{B10}$) functions in native hexamer assembly to coordinate the two axial zinc ions in the central axis of the hexamer. Substitution of $His^{B10}$ by Asp impairs the binding of zinc ions in this axial mode and blocks higher-order self-assembly via the trimer-related surface of the classical hexamer. $Asp^{B10}$ may be expected on general grounds by enhance the segmental stability of the central B-chain α-helix in the zinc-free monomer or dimer via electrostatic mechanisms: as a favorable C-Cap residue and through potential formation of an (i, i+4) salt bridge (with $Glu^{B14}$). Irrespective of the theoretical underpinnings of protein stability, substitution of $His^{B10}$ by Asp was observed indeed to augment the thermodynamic stability of the zinc-free insulin monomer as probed by chemical-denaturation studies. $Asp^{B10}$ also enhances the affinity of insulin for the insulin receptor and augments in parallel its potency to stimulate lipogenesis in isolated adipocytes. Despite the above favorable properties conferred by substitution of $His^{B10}$ by Asp in wild-type insulin, its clinical use was precluded by increased mitogenicity in cell-culture assays of neoplastic cell lines (including a cell line derived from a human breast cancer) in association with the finding of an excess incidence of mammary tumors on chronic treatment of Sprague-Dawley rats by $Asp^{B10}$-insulin relative to wild-type insulin. The present invention excludes the use of $Asp^{B10}$ as a stabilizing substitution due to its unfavorable association with carcinogenesis in Sprague-Dawley rats. The present invention also excludes artificial amino acids known in the art to enhance the thermodynamic stability of globular proteins or non-polar peptide interfaces (such as fluorinated aliphatic or aromatic side chains) as such unnatural amino acids are associated with elevated manufacturing costs and unknown toxicity in medical products intended for long-term use in patients or human subjects.

SUMMARY OF THE INVENTION

It is, therefore, an aspect of the present invention to provide an insulin analogue having enhanced thermodynamic stability in a zinc-free solution while exhibiting decreased self-association, particularly at higher concentrations, such as those greater than 0.6 mM, and while maintaining at least 20 percent of the biological potency of wild-type human insulin on a nanomolar basis. It is another aspect of the present invention that the insulin analogue does not exhibit enhanced mitogenicity. It is a further aspect that insulin analogue can be designed to exhibit sufficient zinc-free stability so as to confer resistance to chemical degradation and resistance to physical degradation—and therefore enable the development of rapid-acting pharmaceutical formulations on subcutaneous injection at strengths U-100-U-300 and in some cases as high as U-500. It is still another aspect that such stability can be obtained in the absence of the cancer-associated $Asp^{B10}$ substitution and in the absence of artificial amino acids. The absence of the need for zinc ions and the increased intrinsic stability of these analogues will permit a broad range of excipients to be feasible, including excipients that enhance the absorption of the injected insulin analogue from the subcutaneous depot into the bloodstream. It is further envisioned that the present combination of stabilizing elements confers sufficient stability to permit the additional incorporation of substitutions at sites designed to foreshorten the duration of insulin signaling once the insulin receptor is engaged. We envisage that the products of the present invention will disproportionately benefit patients treated with continuous subcutaneous infusion via insulin pumps and further may enable the miniaturization of such pumps.

The analogues of the present invention thus consist of two polypeptide chains that contain a novel combination of amino-acid substitutions such that the analogues exhibit (i) enhanced thermodynamic stability in a zinc-free solution, (ii) decreased self-association at protein concentrations greater than 0.6 mM, and (iii) biological potency at least 20% of that of wild-type human insulin on a nanomolar basis in a diabetic rat. To these ends, the analogues of the present invention contain novel combinations of (i) stabilizing substitutions (at positions A8, A14, and/or B29), (ii) a modification that augments physical stability (N-terminal B-chain deletions of one, two or three residues), optionally with (iii) substitutions near the N terminus of the B chain and/or at position A21 that enhance chemical stability; and additionally optionally (iv) substitutions at or adjoining the "Site 2"-related surface of insulin (positions B13, B17, B18, A12, A13, A14 and/or A17) designed to foreshorten the duration of signaling once the insulin receptor is engaged. The latter substitutions may be stabilizing or destabilizing such that the combination of substitutions and modifications provides an analogue whose thermodynamic stability is greater than that of WT insulin. The analogues of the present invention may optionally contain one- or two-residue extensions of the B chain (residues B31 and B32). Specifically excluded are unnatural amino acids and the mitogenic substitution $Asp^{B10}$.

It is envisioned that the present invention can provide a medical benefit in the form of optimization of the pharmacokinetic properties of a soluble insulin analogue formulation such that rapid onset of action is retained in formulations of strengths in the range U-200 through U-1000, i.e., between twofold and tenfold higher than conventional U-100 insulin products (in this nomenclature "U-X" designates X internal units per ml of solution or suspension).

We envisage that insulin analogues and formulations of the present invention will have utility in the treatment of diabetes mellitus. It is, therefore, an aspect of the present invention that analogues containing a combination of amino-acid substitutions and/or N-terminal B-chain deletions, as set forth herein, that enable its stable formulation in a zinc-free solution at neutral pH in the protein concentration range 0.6-6.0 mM such that "rapid action" is maintained following subcutaneous injection in an animal model of diabetes mellitus—"rapid action" being defined by the reference pharmacodynamics profile of Humalog® or Apidra® at a protein concentration 0.6 mM (i.e., as in a standard U-100 insulin product) on subcutaneous injection in the same animal model. It is an additional aspect of the present invention that the analogues exhibit thermodynamic stabilities, chemical stabilities and physical stabilities equal to or greater than that of insulin lispro or insulin glulisine (the active components of Humalog® or Apidra®, respectively) when dissolved in a solution at neutral pH in the absence of zinc ions or other divalent metal ions. It is another aspect of the present invention that the analogues exhibit mitogenicities in a tissue-culture assay of a human breast-cancer cell line and also mediate transcriptional activation of the cell-proliferation-associated cyclin-D1 gene that in each case are equal to or less than that of insulin lispro (KP-insulin). It is yet another aspect of the present invention to provide a method of recombinant manufacture of insulin analogs containing N-terminal deletion of residues B1, B1-B2 or B1-B3, optionally in conjunction with substitutions at neighboring positions to retard their chemical degradation.

In general, the present invention provide insulin analogues that each contain multiple modifications (but excluding substitutions at position B10 and without incorporation of unnatural amino acids) that together confer rapid action under a broad range of protein concentrations in the range 0.6-6 mM and that together are compatible with stable pharmaceutical formulation in the absence of zinc ions or other divalent metal ions. Substitutions are located at one or more of the following positions: A8, A14, A17, B2, B3, B28 and/or B29. The analogs may optionally contain N-terminal deletion of the B chain (up to and including B3) and substitutions at or near the new N terminus to mitigate chemical degradation. The present invention thus pertains to a novel class of insulin analogues containing a combination of modifications that together provide the long-sought clinical advantages not conferred by any one of the constituent modifications. In another version of the present invention residue B30 is absent. In yet another embodiment, the analogue of the present invention may contain Glycine, Alanine or Aspartic Acid at position A21.

DETAILED DESCRIPTION OF THE INVENTION

Figure 1A:
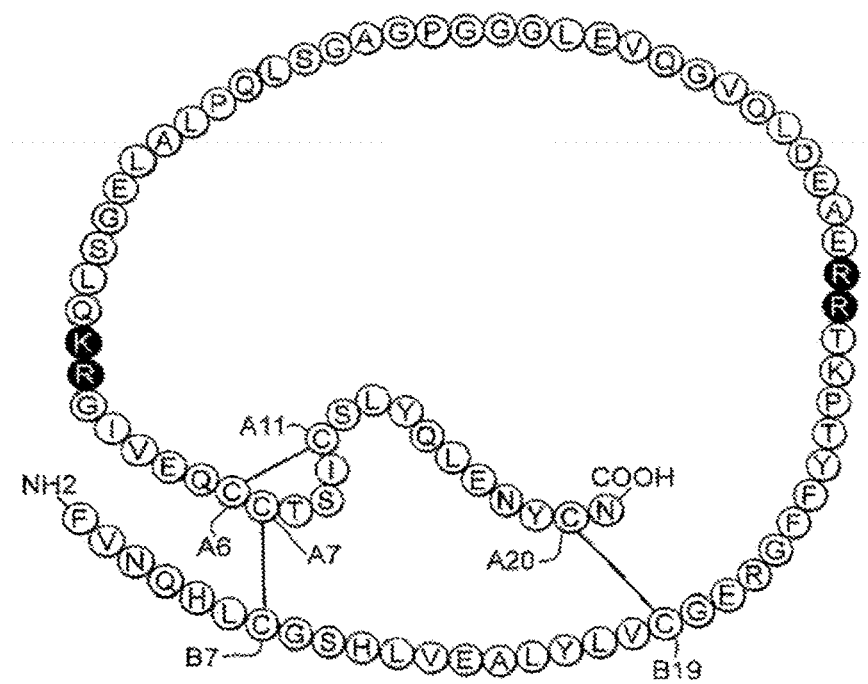
FIG. 1A is a schematic representation of the sequence of human proinsulin (SEQ ID NO: 1) including the A- and B-chains and the connecting region shown with flanking dibasic cleavage sites (filled circles) and C-peptide (open circles).
Figure 1B:
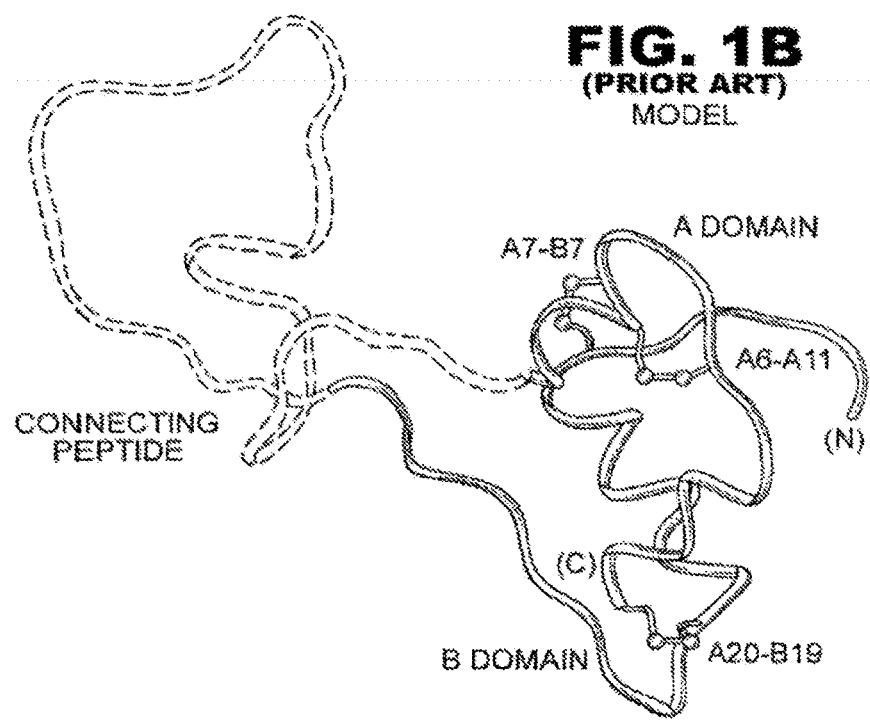
FIG. 1B is a structural model of proinsulin, consisting of an insulin-like moiety and a disordered connecting peptide (dashed line).
Figure 1C:
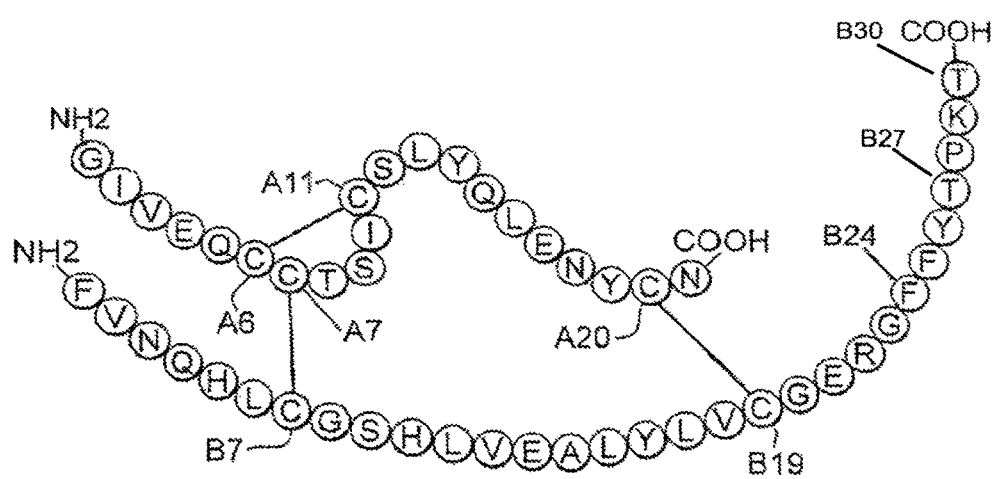
FIG. 1C is a schematic representation of the sequence of human insulin indicating the position of residues B27 and B30 in the B-chain. The top chain is the insulin A-chain (SEQ ID NO: 2) and the bottom chain is the insulin B-chain (SEQ ID NO: 3).
Figure 2:
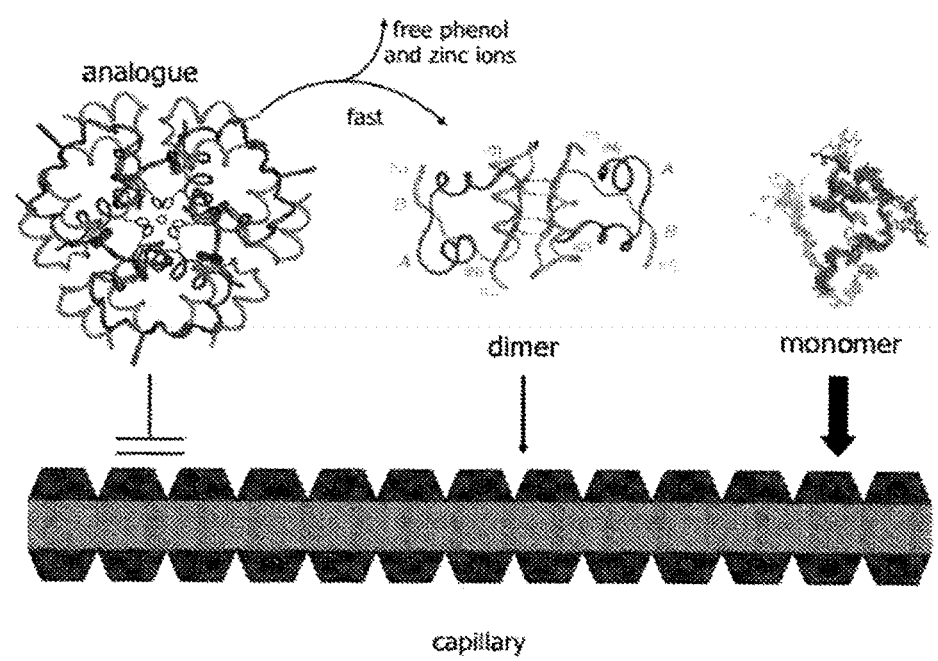
FIG. 2 is a schematic representation prandial (rapid-acting) insulin analogs as known in the art, including the insulin hexamer (upper left), the insulin dimer (center top) and insulin monomer (upper right) with a representation of the ability of each of these forms to efficiently penetrate into capillaries (bottom).

The present invention is directed toward an insulin analogue that provides enhanced in vivo biological potency on a per-molecular basis, rapid action under a broad range of protein concentrations and formulation strengths (typically from U-100 to U-500, and optionally as high as U-1000), IR-A/IR-B receptor-binding affinities with absolute affinities in the range 5-100% relative to the affinities of wild-type human (the lower limit chosen to correspond to proinsulin), affinity for the IGF-1R no greater than that of insulin lispro, and thermodynamic stability in the absence of zinc ions that is equal to or greater than that of human insulin lispro in the absence of zinc ions.

The above combination of features is conferred by a novel combination of substitutions within the A- and B chains, optionally with N-terminal deletion of the B chain, and optionally des-Thr$^{B30}$. The A- and B chain substitutions fall into five classes: (i) substitutions at Site-related positions (B13, B17, B18, A12, A13, A14 and/or A17); (ii) non-beta-branched substitutions at position A8; (iii) helicogenic substitutions at position A14 containing side chains that are either polar, charged or smaller than the native Tyrosine; (iv) substitutions at positions B28 and/or B29 as known in the art to decrease dimerization of insulin or to enhance its solubility at neutral pH; and (v) substitutions near the N terminus of the B chain in conjunction with N-terminal deletions. Some of these substitutions may in isolation augment the stability of wild-type insulin whereas others may in isolation impair the stability of wild-type insulin. Likewise, some of these substitutions may in isolation extend the tail of insulin action (on intravenous bolus injection) whereas others may in isolation mitigate or foreshorten this tail. An aspect of the invention provides a combination of such substitutions, optionally in conjunction with N-terminal deletion of the B chain, that together provide an insulin analogue whose formulation under a broad range of protein concentrations in the range 0.6-6.0 mM retains rapid action on subcutaneous injection and exhibits adequate physical- and chemical stability to be practical for the treatment of diabetes mellitus.

Optimization of the C-CAP Residue of the A1-A8 α-Helix. The β-branched side chain of Threonine at position A8 violates peptide-based rules of α-helical propensity and C-CAP potential. Thr$^{A8}$ is near but not within the classical receptor-binding surface of insulin as defined in co-crystal structures of insulin bound to fragments of the receptor ectodomain. Non-β-branched substitutions at this position are known in the art to stabilize the insulin molecule in the context of wild-type insulin and insulin lispro, but their functional compatibility and biophysical effects on insulin analogues containing Site-2-related substitutions are unknown and difficult to predict because effects of C-CAP substitutions in globular proteins are in general context dependent.

Optimization of the Surface of the A12-A18 α-Helix. An unusual feature of the structure of the insulin monomer is the hyper-exposure of Tyrosine at position A14 on the surface of the A12-A18 α-helix. The conformation of this side chain is variable among crystal structures and exhibits motional narrowing in $^1$H-NMR studies under a variety of solution conditions. Substitution of such an exposed large non-polar side chain by a side chain of similar helical propensity that is smaller (such as Alanine), polar (such as Glutamine), or charged (such as Glutamic Acid or Arginine) might enhance overall stability by mitigating the reverse hydrophobic effect, but like C-CAP potential above, this effect is context-dependent and highly variable in magnitude. Too few examples of reverse hydrophobic effects have been described to enable effects of A14 substitutions on the stability of insulin to be predictable.

The N-terminal three residues of the B chain exhibit variable or disordered conformations. Although deletion of residues B1, B1-B2 or B1-B3 of the B chain of insulin is known in the art not to impair the activity of insulin or its binding of the hormone to the insulin receptor, this "arm" contributes to the nascent folding efficiency of proinsulin within mammalian cells. Whereas such deletions do not alter the thermodynamic stability of the mature zinc-free hormone in solution, such deletions eliminate the solvent exposure of non-polar side chains (Phenylalanine at position B1 and Valine at position B2) and so may reduce the tendency of the protein to undergo non-native aggregation, extending physical stability. Because such deletions may enhance the chemical degradation of residues at or near the new N terminus, deletion of residues B1, B1-B2 or B1-B3 may optionally be combined with neighboring amino-acid substitutions intended to mitigate such chemical degradation in a neutral-pH solution. Also without wishing to be constrained by theory, we further envision that additive or non-additive effects of Site-2-related substitutions and $Glu^{B29}$ attenuate mitogenic signaling by such analogues on binding to the insulin receptor and would be associated with reduced binding to the mitogenic Type 1 IGF receptor.

It is an aspect of the present invention that rapid absorption kinetics from a subcutaneous depot may be generated by an insulin analogue that is monomeric, dimeric, trimeric, tetrameric or hexameric—but not is a higher-order state of self-assembly—in a zinc-free solution at neutral pH at a protein concentration of 0.6-6.0 mM (as calculated in relation to the formal monomer concentration). In the absence of zinc ions or other divalent metal ions, such native self-association is characterized by rapid exchange among states of self-assembly (i.e., with rate constants of dissociation such that lifetimes of the component dimers, trimers, tetramers and hexamers, to the extent that they are present in the equilibrium, are less than 1 second). Such rapid exchange stands in contrast to lifetimes of hours observed among zinc-stabilized insulin hexamers. Conventional prandial products, as known in the art, represent a continuum of possible coupled equilibria between states of self-assembly, including zinc-stabilized or zinc-ion-independent hexamers extended by potential hexamer-hexamer interactions. Molecular implementation of this strategy provides a novel class of insulin analogues that (i) are as stable or more stable as a zinc-free monomer and dimer relative to insulin lispro and (ii) retain at least a portion of the biological potency of wild-type human insulin (as assessed by hormone-regulated reduction in blood-glucose concentration) on a per-molecular or per-nanomole basis. It is a feature of the present invention that retained potency in relation to glycemic control is associated with a mitogenicity that is no higher than that of insulin lispro. For many of the analogues of the present invention, mitogenicity is reduced relative to wild-type insulin, a reduction that is a biological consequence of a distinct signaling pathway that is undesirable from the perspective of cancer risk and cancer growth.

It is also envisioned that insulin analogues may be made with A- and B chain sequences derived from animal insulins, such as porcine, bovine, equine, and canine insulins, by way of non-limiting examples, so long as no substitutions are present at position B10 and no unnatural amino acids are utilized. Such variant B chains derived from human insulin or animal insulins may optionally lack $Thr^{B30}$ (des-B30) or contain a C-terminal dipeptide extension (with respective residue positions designated B31 and B32) wherein at least one of these C-terminal extended residues is an acidic amino acid. In addition or in the alternative, the insulin analogue of the present invention may contain a deletion of residues B1, B1-B2, or B1-B3; or may be combined with a variant B chain lacking Proline at position B28 (e.g., $LyS^{B28}$, $Ala^{B28}$ or $Gln^{B28}$ in combination with Glutamic Acid at position B29).

It is further envisioned that the insulin analogues of the present invention may be derived from Lys-directed proteolysis of a precursor polypeptide in yeast biosynthesis in *Pichia pastoris, Saccharomyces cerevisciae*, or other yeast expression species or strains. Such strains may be engineered to encode a Lysine at positions B1, B2 or B3 in order to enable post-fermentation processing of a precursor containing an N-terminal B-chain extension such that analogues respectively lacking residues B1, B1-B2 or B1-B3 are produced. The new N-terminal residue may optionally be substituted by Glutamic Acid or Alanine. The variant B chain of a des-B1 analogue may therefore begin with an N-terminal Valine (the native B2 residue in wild-type insulin), Alanine or Glutamic Acid and optionally Alanine or Glutamic Acid at the second position; the variant B chain of a des-[B1-B2] analogue may likewise begin with an N-terminal Asparagine (the native B2 residue in wild-type insulin), Alanine or Glutamic Acid at the first position and optionally Alanine or Glutamic Acid at the second position; the variant B chain of a des-[B1-B3] analogue may likewise begin with an N-terminal Glutamine (the native B3 residue in wild-type insulin), Alanine or Glutamic Acid. Such substitutions at or adjoining the new N terminus of variant B chain are intended to avoid chemical degradation of Asparagine at wild-type position B3 and Glutamine at wild-type position B4. Such substitution of Glutamic Acid would also augment the net negative charge of the insulin analogue at neutral pH, which would be expected to enhance its solubility at neutral pH.

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Acidic amino acids are Aspartic acid (Asp or D) and Glutamic acid (Glu or E). Introduction of basic amino-acid substitutions (including Lysine (Lys or K), Arginine (Arg or R) and Histidine (His or H)) are not preferred in order to maintain the enhanced net negative charge of this class of analogues. Unless noted otherwise or wherever obvious from the context, the amino acids noted herein should be considered to be L-amino acids. Standard amino acids may also be substituted by non-standard amino acids belonging to the same chemical class.

The amino-acid sequence of human proinsulin is provided, for comparative purposes, as SEQ ID NO: 1.

```
(human proinsulin)
                                        SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn
```

The amino-acid sequence of the A chain of human insulin is provided as SEQ ID NO: 2.

```
(human A chain; residue positions A1-A21)
                                        SEQ ID NO: 2
Gly-Ile-Val-Glu-Gln-Cys-Cys-Thr-Ser-Ile-Cys-Ser- Leu-Tyr-Gln-Leu-Glu-Asn-Tyr-Cys-Asn
```

The amino-acid sequence of the B chain of human insulin is provided as SEQ ID NO: 3.

```
(human B chain; residue positions B1-B30)
                                        SEQ ID NO: 3
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The amino-acid sequence of a modified insulin of the present invention is given in general form in SEQ ID NO 4 and SEQ ID NO: 5 wherein the six Cysteine residues are paired to provide three disulfide bridges as in wild-type human insulin.

```
     A chain
                                        SEQ ID NO: 4
Gly-Ile-Val-Glu-Gln-Cys-Cys-Xaa₁-Ser-Ile-Cys- Xaa₂-Xaa₃-Xaa₄-Gln-Leu-Xaa₅-Asn-Tyr-Cys-Xaa₆
```

```
     B chain
                                        SEQ ID NO: 5
Xaa₇-Xaa₈-Xaa₉-Xaa₁₀-His-Leu-Cys-Gly-Ser-His- Leu-Ala-Xaa₁₁-Ala-Leu-Tyr-Xaa₁₂-Xaa₁₃-Cys-Gly- Glu-Arg-Gly-Phe-Phe-Tyr-Thr-Xaa₁₄-Xaa₁₅-Thr- Xaa₁₆-Xaa₁₇
```

Where $Xaa_1$ (position A8) may be Thr (as in wild-type insulin), His, Glu or any other non-β-branched amino acid; where $Xaa_2$ may be Ser (as in wild-type insulin), Ala, Asp, Glu or His; where $Xaa_3$ may be Leu (as in wild-type insulin), Ala, Glu, His, Phe, Tyr or Trp; where $Xaa_4$ may be Tyr (as in wild-type insulin), Ala, Glu, Gln, His or Leu; where $Xaa_5$ may be Glu (as in wild-type insulin), Ala, Arg, Gln, His, Leu, Phe or Tyr; where $Xaa_6$ may be Asn (as in wild-type insulin), Ala, Gly or Glu; where $Xaa_7$-$Xaa_8$-$Xaa_9$ may be Phe-Val-Asn as in wild-type human insulin or N-terminal deleted variants Val-Asn (des-B1; no residue $Xaa_7$), Asn (des-B1, B2; no residue $Xaa_7$ and no residue $Xaa_8$) or omitted (des-B1-B3; no residue $Xaa_7$, no residue $Xaa_8$ and no residue $Xaa_9$), or optionally a respective des-B1 variant (beginning Ala-Asn, Glu-Asn, Ala-Ala, Ala-Glu or Glu-Glu), a des-B1, B2 variant (beginning Asn-Glu, Asn-Ala, Ala-Asn, Glu-Asn, Ala-Ala, Ala-Glu, Glu-Ala or Glu-Glu), or a des-B1-B3 variant (beginning Ala-His or Glu-His); where $Xaa_{10}$ may be Gln (as in wild-type insulin), Ala or Glu; where $Xaa_{11}$ may be Glu (as in wild-type insulin), Ala, Gln, His or Leu; where $Xaa_{12}$ may be Leu (as in wild-type insulin), Ala, Arg, Glu, His, Lys, Phe, Trp, Tyr or Val; where $Xaa_{13}$ may be Val (as in wild-type insulin), Ala, His, Leu, Lys, Glu, Phe, Thr, Trp or Tyr; where $Xaa_{14}$ may be Pro (as in wild-type insulin), Ala, Arg, Glu, or Lys; where $Xaa_{15}$ may be Lys (as in wild-type insulin), Ala, Arg, Glu, or Pro; and where optionally $Xaa_{16}$-$Xaa_{17}$ provides a C-terminal monopeptide or dipeptide extension of the B chain such that at least one residue is an acidic side chain (Asp or Glu). Analogues of the present invention may lack C-terminal extention $Xaa_{16}$-$Xaa_{17}$ and also lack $Thr^{B30}$ (or any other amino acid) at position B30.

Thus, analogues of the present invention may optionally contain N-terminal deletions of the B chain (des-B1, des-B1, B2 or des-B1-B3) as indicated in SEQ ID NOs: 6-26. These N-terminal residues are not required for receptor binding, but their presence in a biosynthetic single-chain precursor is thought to enhance the efficiency of native disulfide pairing in the endoplasmic reticulum and thus production yields. By way of non-limiting examples, the following sequences exemplify variant B chains containing N-terminal deletions.

Examples of specific A-chain and B-chain sequences according to the present invention include SEQ ID NOs: 6-104.

```
SEQ ID NO 6: des-(B1) derivative of Glu^{B28}-
insulin
Val-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Glu-Lys-Thr
```

SEQ ID NO 7: des-(B1, B2) derivative of Glu$^{B28}$-
insulin
Asn-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Glu-Lys-Thr SEQ ID NO 8: des-(B1-B3) derivative of Glu$^{B28}$-
insulin
Gln-His-Leu-Cys-Gly-Ser-His-Leu-Val-Glu-Ala-Leu- Tyr-Leu-Val-Cys-Gly-Glu-Arg-Gly-Phe-Phe-Tyr-Thr- Glu-Lys-Thr SEQ ID NO 9: des-(B1) derivative of Asp$^{B28}$-
insulin
Val-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Asp-Lys-Thr SEQ ID NO 10: des-(B1, B2) derivative of Asp$^{B28}$-
insulin
Asn-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Asp-Lys-Thr SEQ ID NO 11: des-(B1-B3) derivative of Asp$^{B28}$-
insulin
Gln-His-Leu-Cys-Gly-Ser-His-Leu-Val-Glu-Ala-Leu- Tyr-Leu-Val-Cys-Gly-Glu-Arg-Gly-Phe-Phe-Tyr-Thr- Asp-Lys-Thr SEQ ID NO 12: des-(B1) derivative of (Lys$^{B28}$,
Pro$^{B29}$)-insulin
Val-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Lys-Pro-Thr SEQ ID NO 13: des-(B1, B2) derivative of (Lys$^{B28}$,
Pro$^{B29}$)-insulin
Asn-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Lys-Pro-Thr SEQ ID NO 14: des-(B1-B3) derivative of (Lys$^{B28}$,
Pro$^{B29}$)-insulin
Gln-His-Leu-Cys-Gly-Ser-His-Leu-Val-Glu-Ala-Leu- Tyr-Leu-Val-Cys-Gly-Glu-Arg-Gly-Phe-Phe-Tyr-Thr- Lys-Pro-Thr SEQ ID NO 15: des-(B1) derivative of (Ala$^{B28}$)-
insulin
Val-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Ala-Lys-Thr SEQ ID NO 16: des-(B1, B2) derivative of
(Ala$^{B28}$)-insulin
Asn-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Ala-Lys-Thr SEQ ID NO 17: des-(B1-B3) derivative of (Ala$^{B28}$)-
insulin
Gln-His-Leu-Cys-Gly-Ser-His-Leu-Val-Glu-Ala-Leu- Tyr-Leu-Val-Cys-Gly-Glu-Arg-Gly-Phe-Phe-Tyr-Thr- Ala-Lys-Thr SEQ ID NO 18: des-(B1) derivative of (Glu$^{B28}$,
Pro$^{B29}$)-insulin
Val-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Glu-Pro-Thr SEQ ID NO 19: des-(B1, B2) derivative of (Glu$^{B28}$,
Pro$^{B29}$)-insulin
Asn-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Glu-Pro-Thr SEQ ID NO 20: des-(B1-B3) derivative of (Glu$^{B28}$,
Pro$^{B29}$)-insulin
Gln-His-Leu-Cys-Gly-Ser-His-Leu-Val-Glu-Ala-Leu- Tyr-Leu-Val-Cys-Gly-Glu-Arg-Gly-Phe-Phe-Tyr-Thr- Glu-Pro-Thr SEQ ID NO 21: des-(B1) derivative of (Ala$^{B28}$,
Pro$^{B29}$)-insulin
Val-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Ala-Pro-Thr SEQ ID NO 22: des-(B1, B2) derivative of (Ala$^{B28}$,
Pro$^{B29}$)-insulin
Asn-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Ala-Pro-Thr SEQ ID NO 23: des-(B1-B3) derivative of (Ala$^{B28}$,
Pro$^{B29}$)-insulin
Gln-His-Leu-Cys-Gly-Ser-His-Leu-Val-Glu-Ala-Leu- Tyr-Leu-Val-Cys-Gly-Glu-Arg-Gly-Phe-Phe-Tyr-Thr- Ala-Pro-Thr The insulin analogues of the present invention containing variant B chains with the above N-terminal deletions may also contain amino-acid substitutions at or near the new N terminus as exemplified in the following sequences as non-limiting examples.

SEQ ID NO 24: des-(B1) derivative of Glu$^{B28}$-
insulin in which the variant B chain begins Ala-
Asn, Glu-Asn, Val-Ala, Val-Glu, Glu-Ala, or Glu-
Glu.
Xaa-Xaa-Val-Asn-Gln-His-Leu-Cys-Gly-Ser-His-Leu- Val-Glu-Ala-Leu-Tyr-Leu-Val-Cys-Gly-Glu-Arg-Gly- Phe-Phe-Tyr-Thr-Glu-Lys-Thr SEQ ID NO 25: des-(B1, B2) derivative of Glu$^{B28}$-
insulin in which the variant B chain begins Asn-
Glu, Asn-Ala, Ala-Gln, Glu-Gln, Ala-Glu, Glu-
Glu, or Glu-Ala.
Xaa-Xaa-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Glu-Lys-Thr SEQ ID NO 26: des-(B1-B3) derivative of Glu$^{B28}$-
insulin in which the new N-terminal residue is
Ala or Glu.
Xaa-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Glu-Lys-Thr SEQ ID NO 27: des-(B1) derivative of Asp$^{B28}$-
insulin in which the variant B chain begins Ala-
Asn, Glu-Asn, Val-Ala, Val-Glu, Glu-Ala, or Glu-
Glu.
Xaa-Xaa-Val-Asn-Gln-His-Leu-Cys-Gly-Ser-His-Leu- Val-Glu-Ala-Leu-Tyr-Leu-Val-Cys-Gly-Glu-Arg-Gly- Phe-Phe-Tyr-Thr-Asp-Lys-Thr SEQ ID NO 28: des-(B1, B2) derivative of Asp$^{B28}$-
insulin in which the variant B chain begins Asn-
Glu, Asn-Ala, Ala-Gln, Glu-Gln, Ala-Glu, Glu-
Glu, or Glu-Ala.
Xaa-Xaa-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Asp-Lys-Thr SEQ ID NO 29: des-(B1-B3) derivative of Asp$^{B28}$-
insulin in which the new N-terminal residue is
Ala or Glu.
Xaa-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Asp-Lys-Thr SEQ ID NO 30: des-(B1) derivative of (Lys$^{B28}$,
Pro$^{B29}$) insulin in which the variant B chain
begins Ala-Asn, Glu-Asn, Val-Ala, Val-Glu, Glu-
Ala, or Glu-Glu.
Xaa-Xaa-Val-Asn-Gln-His-Leu-Cys-Gly-Ser-His-Leu- Val-Glu-Ala-Leu-Tyr-Leu-Val-Cys-Gly-Glu-Arg-Gly- Phe-Phe-Tyr-Thr-Lys-Pro-Thr SEQ ID NO 31: des-(B1, B2) derivative of (Lys$^{B28}$,
Pro$^{B29}$)-insulin in which the variant B chain
begins Asn-Glu, Asn-Ala, Ala-Gln, Glu-Gln,
Ala-Glu, Glu-Glu, or Glu-Ala.
Xaa-Xaa-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Lys-Pro-Thr SEQ ID NO 32: des-(B1-B3) derivative of (Lys$^{B28}$,
Pro$^{B29}$)-insulin in which the new N-terminal
residue is Ala or Glu.
Xaa-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Lys-Pro-Thr SEQ ID NO 33: des-(B1) derivative of (Glu$^{B28}$)-
insulin in which the variant B chain begins
Ala-Asn, Glu-Asn, Val-Ala, Val-Glu, Glu-Ala, or
Glu-Glu.
Xaa-Xaa-Val-Asn-Gln-His-Leu-Cys-Gly-Ser-His-Leu- Val-Glu-Ala-Leu-Tyr-Leu-Val-Cys-Gly-Glu-Arg-Gly- Phe-Phe-Tyr-Thr-Glu-Lys-Thr SEQ ID NO 34: des-(B1, B2) derivative of
(Ala$^{B28}$)-insulin in which the variant B chain
begins Asn-Glu, Asn-Ala, Ala-Gln, Glu-Gln, Ala-
Glu, Glu-Glu, or Glu-Ala.
Xaa-Xaa-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Ala-Lys-Thr SEQ ID NO 35: des-(B1-B3) derivative of (Ala$^{B28}$)-
insulin in which the new N-terminal residue is
Ala or Glu.
Xaa-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Ala-Lys-Thr SEQ ID NO 36: des-(B1) derivative of (Glu$^{B28}$,
Pro$^{B29}$)-insulin in which the variant B chain
begins Ala-Asn, Glu-Asn, Val-Ala, Val-Glu, Glu-
Ala, or Glu-Glu.
Xaa-Xaa-Val-Asn-Gln-His-Leu-Cys-Gly-Ser-His-Leu- Val-Glu-Ala-Leu-Tyr-Leu-Val-Cys-Gly-Glu-Arg-Gly- Phe-Phe-Tyr-Thr-Glu-Pro-Thr SEQ ID NO 37: des-(B1, B2) derivative of (Glu$^{B28}$,
Pro$^{B29}$)-insulin in which the variant B chain
begins Asn-Glu, Asn-Ala, Ala-Gln, Glu-Gln, Ala-
Glu, Glu-Glu, or Glu-Ala.
Xaa-Xaa-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Glu-Pro-Thr SEQ ID NO 38: des-(B1-B3) derivative of (Glu$^{B28}$,
Pro$^{B29}$)-insulin in which the new N-terminal
residue is Ala or Glu.
Xaa-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Glu-Pro-Thr SEQ ID NO 39: des-(B1) derivative of (Ala$^{B28}$,
Pro$^{B29}$)-insulin in which the variant B chain
begins Ala-Asn, Glu-Asn, Val-Ala, Val-Glu, Glu-
Ala, or Glu-Glu.
Xaa-Xaa-Val-Asn-Gln-His-Leu-Cys-Gly-Ser-His-Leu- Val-Glu-Ala-Leu-Tyr-Leu-Val-Cys-Gly-Glu-Arg-Gly- Phe-Phe-Tyr-Thr-Ala-Pro-Thr SEQ ID NO 40: des-(B1, B2) derivative of (Ala$^{B28}$,
Pro$^{B29}$)-insulin in which the variant B chain
begins Asn-Glu, Asn-Ala, Ala-Gln, Glu-Gln, Ala-
Glu, Glu-Glu, or Glu-Ala.
Xaa-Xaa-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Ala-Pro-Thr SEQ ID NO 41: des-(B1-B3) derivative of (Ala$^{B28}$, Pro$^{B29}$)-insulin in which the new N-terminal residue is Ala or Glu.
Xaa-Gln-His-Leu-Cys-Gly-Ser-His-Leu-Val-Glu-Ala- Leu-Tyr-Leu-Val-Cys-Gly-Glu-Arg-Gly-Phe-Phe-Tyr- Thr-Ala-Pro-Thr Still further examples of A-chain and B-chain polypeptides according to the present invention include the following:

SEQ ID NO: 42 (HA8 EA14 QA17):
Gly-Ile-Val-Glu-Gln-Cys-Cys-His-Ser-Ile-Cys-Ser-

Leu-Glu-Gln-Leu-Gln-Asn-Tyr-Cys-Asn

SEQ ID NO: 43 (des B1 AB2 EB29):
Ala-Asn-Gln-His-Leu-Cys-Gly-Ser-His-Leu-Val-Glu- Ala-Leu-Tyr-Leu-Val-Cys-Gly-Glu-Arg-Gly-Phe-Phe- Tyr-Thr-Pro-Gl SEQ ID NO: 65 (des B1 EB2 NB17 des B30):
Glu-Asn-Gln-His-Leu-Cys-Gly-Ser-His-Leu-Val-Glu-
Ala-Leu-Tyr-Asn-Val-Cys-Gly-Glu-Arg-Gly-Phe-Phe-
Tyr-Thr-Pro-Lys SEQ ID NO: 66 (des B1 AB2 EB17 des B30):
Ala-Asn-Gln-His-Leu-Cys-Gly-Ser-His-Leu-Val-Glu-
Ala-Leu-Tyr-Glu-Val-Cys-Gly-Glu-Arg-Gly-Phe-Phe-
Tyr-Thr-Pro-Lys SEQ ID NO: 67 (des B1 AB2 FB17 des B30):
Ala-Asn-Gln-His-Leu-Cys-Gly-Ser-His-Leu-Val-Glu-
Ala-Leu-Tyr-Phe-Val-Cys-Gly-Glu-Arg-Gly-Phe-Phe-
Tyr-Thr-Pro-Lys SEQ ID NO: 68 (des [B1, B2] EB29)
Asn-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Glu-Thr SEQ ID NO: 69 (des [B1, B2] des B30):
Asn-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys SEQ ID NO: 70 (des [B1, B2] QB13 des B30):
Asn-Gln-His-Leu-Cys-Gly-Ser-His-Leu-Val-Gln-Ala-
Leu-Tyr-Leu-Val-Cys-Gly-Glu-Arg-Gly-Phe-Phe-Tyr-
Thr-Pro-Lys SEQ ID NO: 71 (des [B1, B2], QB13 EB29)
Asn-Gln-His-Leu-Cys-Gly-Ser-His-Leu-Val-Gln-Ala-
Leu-Tyr-Leu-Val-Cys-Gly-Glu-Arg-Gly-Phe-Phe-Tyr-
Thr-Pro-Glu-Thr SEQ ID NO: 72 (des [B1, B2] QB13 EB22 des B30):
Asn-Gln-His-Leu-Cys-Gly-Ser-His-Leu-Val-Gln-Ala-
Leu-Tyr-Leu-Val-Cys-Gly-Glu-Glu-Gly-Phe-Phe-Tyr-
Thr-Pro-Lys SEQ ID NO: 73 (des [B1, B2] EB 22 des B30):
Asn-Gln-His-Leu-Cys-Gly-Ser-His-Leu-Val-Glu-Ala-
Leu-Tyr-Leu-Val-Cys-Gly-Glu-Glu-Gly-Phe-Phe-Tyr-
Thr-Pro-Lys SEQ ID NO: 74 (EA8 LA14 QA17):
Gly-Ile-Val-Glu-Gln-Cys-Cys-Glu-Ser-Ile-Cys-Ser-
Leu-Leu-Gln-Leu-Gln-Asn-Tyr-Cys-Asn SEQ ID NO: 75 (HA8)
Gly-Ile-Val-Glu-Gln-Cys-Cys-His-Ser-Ile-Cys-Ser-
Leu-Tyr-Gln-Leu-Glu-Asn-Tyr-Cys-Asn SEQ ID NO: 76 (EA8 LA14)
Gly-Ile-Val-Glu-Gln-Cys-Cys-Glu-Ser-Ile-Cys-Ser-
Leu-Leu-Gln-Leu-Glu-Asn-Tyr-Cys-Asn SEQ ID NO: 77 (EA8 EA14)
Gly-Ile-Val-Glu-Gln-Cys-Cys-Glu-Ser-Ile-Cys-Ser-
Leu-Glu-Gln-Leu-Glu-Asn-Tyr-Cys-Asn SEQ ID NO: 78 (EA8 QA17)
Gly-Ile-Val-Glu-Gln-Cys-Cys-Glu-Ser-Ile-Cys-Ser-
Leu-Tyr-Gln-Leu-Gln-Asn-Tyr-Cys-Asn SEQ ID NO: 79 (EA8 WA13 EA14)
Gly-Ile-Val-Glu-Gln-Cys-Cys-Glu-Ser-Ile-Cys-Ser-
Trp-Glu-Gln-Leu-Glu-Asn-Tyr-Cys-Asn SEQ ID NO: 80 (HA8 WA13 EA14)
Gly-Ile-Val-Glu-Gln-Cys-Cys-His-Ser-Ile-Cys-Ser-
Trp-Glu-Gln-Leu-Glu-Asn-Tyr-Cys-Asn SEQ ID NO: 81 (des [B1, B2] AB3 des B30):
Ala-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys SEQ ID NO: 82 (des [B1, B2] EB3 des B30):
Glu-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Lys SEQ ID NO: 83 (des [B1, B2] EB3 EB29)
Glu-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Glu-Thr SEQ ID NO: 84 (des [B1, B2] AB3 EB29)
Ala-Gln-His-Leu-Cys-Gly-Ser-His-Leu-Val-Glu-Ala-
Leu-Tyr-Leu-Val-Cys-Gly-Glu-Arg-Gly-Phe-Phe-Tyr-
Thr-Pro-Glu-Thr SEQ ID NO: 85 (des [B1, B2] EB3 PB17 des B30):
Glu-Gln-His-Leu-Cys-Gly-Ser-His-Leu-Val-Glu-Ala-
Leu-Tyr-Phe-Val-Cys-Gly-Glu-Arg-Gly-Phe-Phe-Tyr-
Thr-Pro-Lys SEQ ID NO: 86 (des [B1, B2] EB3 EB17 des B30):
Glu-Gln-His-Leu-Cys-Gly-Ser-His-Leu-Val-Glu-Ala-
Leu-Tyr-Glu-Val-Cys-Gly-Glu-Arg-Gly-Phe-Phe-Tyr-
Thr-Pro-Lys SEQ ID NO: 87 (des [B1, B2] EB3 NB17 des B30):
Glu-Gln-His-Leu-Cys-Gly-Ser-His-Leu-Val-Glu-Ala-
Leu-Tyr-Asn-Val-Cys-Gly-Glu-Arg-Gly-Phe-Phe-Tyr-
Thr-Pro-Lys SEQ ID NO: 88 (des [B1, B2] EB3 FB17 EB29)
Glu-Gln-His-Leu-Cys-Gly-Ser-His-Leu-Val-Glu-Ala-
Leu-Tyr-Phe-Val-Cys-Gly-Glu-Arg-Gly-Phe-Phe-Tyr-
Thr-Pro-Glu-Thr -continued SEQ ID NO: 89 (des [B1-B3] des B30):
Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys SEQ ID NO: 90 (des [B1-B3] QB13 des B30):
Gln-His-Leu-Cys-Gly-Ser-His-Leu-Val-Gln-Ala-Leu-Tyr-Leu-Val-Cys-Gly-Glu-Arg-Gly-Phe-Phe-Tyr-Thr-Pro-Lys SEQ ID NO: 91 (des [B1-B3] EB29)
Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Glu-Thr SEQ ID NO: 92 (des [B1-B3] QB13 EB29)
Gln-His-Leu-Cys-Gly-Ser-His-Leu-Val-Gln-Ala-Leu-Tyr-Leu-Val-Cys-Gly-Glu-Arg-Gly-Phe-Phe-Tyr-Thr-Pro-Glu-Thr SEQ ID NO: 93 (des [B1-B3] QB13 EB22 des B30):
Gln-His-Leu-Cys-Gly-Ser-His-Leu-Val-Gln-Ala-Leu-Tyr-Leu-Val-Cys-Gly-Glu-Glu-Gly-Phe-Phe-Tyr-Thr-Pro-Lys SEQ ID NO: 94 (des [B1-B3] QB13 FB17 des B30):
Gln-His-Leu-Cys-Gly-Ser-His-Leu-Val-Gln-Ala-Leu-Tyr-Phe-Val-Cys-Gly-Glu-Arg-Gly-Phe-Phe-Tyr-Thr-Pro-Lys SEQ ID NO: 95 (des [B1-B3] FB17 des B30):
Gln-His-Leu-Cys-Gly-Ser-His-Leu-Val-Glu-Ala-Leu-Tyr-Phe-Val-Cys-Gly-Glu-Arg-Gly-Phe-Phe-Tyr-Thr-Pro-Lys SEQ ID NO: 96 (des [B1-B3] FB17 EB29)
Gln-His-Leu-Cys-Gly-Ser-His-Leu-Val-Glu-Ala-Leu-Tyr-Phe-Val-Cys-Gly-Glu-Arg-Gly-Phe-Phe-Tyr-Thr-Pro-Glu-Thr SEQ ID NO: 97 (des [B1-B3] QB13 FB17 EB29)
Gln-His-Leu-Cys-Gly-Ser-His-Leu-Val-Gln-Ala-Leu-Tyr-Phe-Val-Cys-Gly-Glu-Arg-Gly-Phe-Phe-Tyr-Thr-Pro-Glu-Thr SEQ ID NO: 98 (des [B1-B3] EB4 des B30):
Glu-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys SEQ ID NO: 99 (des [B1-B3] AB4 des B30):
Ala-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys SEQ ID NO: 100 (des [B1-B3] EB4 EB29)
Glu-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Glu-Thr SEQ ID NO: 101 (des [B1-B3] AB4 EB29)
Ala-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Glu-Thr SEQ ID NO: 102 (des [B1-B3] EB4 FB17 des B30):
Glu-His-Leu-Cys-Gly-Ser-His-Leu-Val-Glu-Ala-Leu-Tyr-Phe-Val-Cys-Gly-Glu-Arg-Gly-Phe-Phe-Tyr-Thr-Pro-Lys SEQ ID NO: 103 (des [B1-B3] EB4 EB17 des B30):
Glu-His-Leu-Cys-Gly-Ser-His-Leu-Val-Glu-Ala-Leu-Tyr-Glu-Val-Cys-Gly-Glu-Arg-Gly-Phe-Phe-Tyr-Thr-Pro-Lys SEQ ID NO: 104 (des B1 KB2 AB3 EB17):
Lys-Ala-Gln-His-Leu-Cys-Gly-Ser-His-Leu-Val-Glu-Ala-Leu-Tyr-Glu-Val-Cys-Gly-Glu-Arg-Gly-Phe-Phe-Tyr-Thr-Pro-Lys-Thr SEQ ID NO: 105 (des B1 KB2 AB3 FB17):
Lys-Ala-Gln-His-Leu-Cys-Gly-Ser-His-Leu-Val-Glu-Ala-Leu-Tyr-Phe-Val-Cys-Gly-Glu-Arg-Gly-Phe-Phe-Tyr-Thr-Pro-Lys-Thr SEQ ID NO: 106 (des B1 KB2 EB3 EB17):
Lys-Glu-Gln-His-Leu-Cys-Gly-Ser-His-Leu-Val-Glu-Ala-Leu-Tyr-Glu-Val-Cys-Gly-Glu-Arg-Gly-Phe-Phe-Tyr-Thr-Pro-Lys-Thr SEQ ID NO: 107 (des B1 KB2 EB3 FB17):
Lys-Glu-Gln-His-Leu-Cys-Gly-Ser-His-Leu-Val-Glu-Ala-Leu-Tyr-Phe-Val-Cys-Gly-Glu-Arg-Gly-Phe-Phe-Tyr-Thr-Pro-Lys-Thr SEQ ID NO: 108 (KB2 AB3 EB17):
Phe-Lys-Ala-Gln-His-Leu-Cys-Gly-Ser-His-Leu-Val-Glu-Ala-Leu-Tyr-Glu-Val-Cys-Gly-Glu-Arg-Gly-Phe-Phe-Tyr-Thr-Pro-Lys-Thr SEQ ID NO: 109 (KB2 AB3 FB17):
Phe-Lys-Ala-Gln-His-Leu-Cys-Gly-Ser-His-Leu-Val-Glu-Ala-Leu-Tyr-Phe-Val-Cys-Gly-Glu-Arg-Gly-Phe-Phe-Tyr-Thr-Pro-Lys-Thr SEQ ID NO: 110 (KB2 EB3 EB17):
Phe-Lys-Glu-Gln-His-Leu-Cys-Gly-Ser-His-Leu-Val-Glu-Ala-Leu-Tyr-Glu-Val-Cys-Gly-Glu-Arg-Gly-Phe-Phe-Tyr-Thr-Pro-Lys-Thr -continued SEQ ID NO: 111 (KB2 EB3 FB17):
Phe-Lys-Glu-Gln-His-Leu-Cys-Gly-Ser-His-Leu-Val- Glu-Ala-Leu-Tyr-Phe-Val-Cys-Gly-Glu-Arg-Gly-Phe- Phe-Tyr-Thr-Pro-Lys-Thr Table 1 below provides a listing of examples of insulin analogues or their proinsulin precursors according to the present invention that have been synthesized or envisioned. A representative sampling of the insulin analogues have been tested for biological activity as shown.

TABLE 1

Examples of Insulin Analogs of the Present Invention

| T- | Structure | Maximum | blood Glucose |
|---|---|---|---|
| 0644 | DesB1 HA8 EA14 EB29 | | |
| 0674 | DesB1 HA8 EA14 desB30 | | |
| 0677 | DesB1 HA8 EA14 desB30 | | |
| 0679 | DesB1 HA8 EA14 EB29 | | |
| 0680 | DesB1 EA8 EA14 QA17 desB30 | 17 | |
| 0681 | DesB1 EA8 EA14 QA17 EB29 | 16 | |
| 0684 | DesB1 EA8 EA14 QA17 QB13 desB30 | | |
| 0685 | DesB1 EA8 EA14 QA17 QB13 EB29 | | |
| 0688 | DesB1 EA8 EA14 RA17 desB30 | 27 | |
| 0689 | DesB1 EA8 EA14 RA17 QB13 EB22 | | |
| 0691 | DesB1 EA8 EA14 RA17 QB13 EB22 | 22 | |
| 0692 | DesB1 HA8 EA14 RA17 EB22 desB30 | | |
| 0694 | DesB1 HA8 EA14 RA17 EB22 desB30 | 24 | |
| 0695 | DesB1 HA8 EA14 QA17 EB2 desB30 | 25 | |
| 0697 | DesB1 EA8 EA14 QA17 QB13 desB30 | 27 | |
| 0701 | DesB1 EA8 EA14 QA17 desB30 | | |
| 0702 | DesB1 EA8 EA14 QA17 EB29 | | |
| 0703 | DesB1 HA8 EA14 QA17 desB30 | | |
| 0704 | DesB1 HA8 EA14 QA17 EB29 | | |
| 0708 | DesB1 EA8 EA14 QA17 EB2 desB30 | 25 | |
| 0711 | DesB1 EA8 EA14 QA17 QB13 EB29 | Yes | |
| 0712 | DesB1 EA8 EA14 QA17 EB2 EB29 | 31 | |
| 0715 | DesB1 HA8 EA14 QA17 AB2 desB30 | 38 | |
| 0719 | DesB1 EA8 EA14 QA17 AB2 desB30 | 43 | |
| 0722 | DesB1 EA8 EA14 RA17 AB2 desB30 | 25 | |
| 0724 | DesB1 HA8 WA13 desB30 | | |
| 0731 | DesB1 EA8 EA14 QA17 EB2 EB29 | | |
| 0732 | DesB1 EA8 EA14 RA17 EB2 desB30 | 28 | |
| 0735 | DesB1 EA8 EA14 RA17 AB2 desB30 | | |
| 0737 | DesB1 HA8 EA14 QA17 AB2 EB29 | 34 | |
| 0740 | DesB1 EA8 EA14 RA17 EB2 desB30 | | |
| 0741 | DesB1 EA8 EA14 RA17 desB30 | | |
| 0749 | DesB1 HA8 LA14 QA17 EB2 desB30 | | |
| 0752 | DesB1 EA8 EA14 QA17 AB2 EB29 | | |
| 0757 | DesB1 EA8 LA14 QA17 EB2 desB30 | | |
| 0759 | DesB1 EA8 WA13 EB2 desB30 | | |
| 0760 | DesB1 EA8 WA13 AB2 desB30 | | |
| 0763 | DesB1 EA8 EB2 EB17 desB30 | | |
| 0765 | DesB1 EA8 EB2 FB17 desB30 | | |
| 0769 | DesB1 EA8 EB2 NB17 desB30 | | |
| 0773 | DesB1 EA8 WA13 EB2 EB29 | | |
| 0779 | DesB1 EA8 LA14 RA17 EB2 desB30 | | |
| 0781 | DesB1 EA8 EA14 RA17 AB2 EB17 | | |
| 0782 | DesB1 EA8 EA14 RA17 AB2 FB17 | | |
| 0645 | des[B1-B2] HA8 EA14 EB29 | | |
| 0675 | des[B1-B2] HA8 EA14 desB30 | 0 | |
| 0682 | des[B1-B2] EA8 EA14 QA17 desB30 | | |
| 0683 | des[B1-B2] EA8 EA14 QA17 EB29 | | |
| 0686 | des[B1-B2] EA8 EA14 QA17 QB13 | 36 | |
| 0687 | des[B1-B2] EA8 EA14 QA17 QB13 EB29 | 17.1 | |
| 0690 | des[B1-B2] EA8 EA14 RA17 QB13 EB22 | 27.5 | |
| 0693 | des[B1-B2] HA8 EA14 RA17 EB22 | 18 | |
| 0706 | des[B1-B2] HA8 EA14 QA17 EB3 desB30 | 36 | |

TABLE 1-continued

Examples of Insulin Analogs of the Present Invention

| T- | Structure | Maximum | blood Glucose |
|---|---|---|---|
| 0707 | des[B1-B2] HA8 EA14 QA17 desB30 | 15 | |
| 0713 | des[B1-B2] EA8 EA14 RA17 desB30 | | |
| 0716 | des[B1-B2] HA8 EA14 QA17 AB3 desB30 | 43 | |
| 0720 | des[B1-B2] EA8 EA14 QA17 AB3 desB30 | | |
| 0723 | des[B1-B2] EA8 EA14 QA17 des[B1-B2] | | |
| 0725 | des[B1-B2] EA8 EA14 RA17 EB3 desB30 | | |
| 0728 | des[B1-B2] HA8 EA14 QA17 EB29 | | |
| 0729 | des[B1-B2] HA8 EA14 QA17 EB3 EB29 | | |
| 0734 | des[B1-B2] EA8 EA14 RA17 AB3 desB30 | | |
| 0743 | des[B1-B2] EA8 EA14 QA17 EB3 EB29 | | |
| 0744 | des[B1-B2] EA8 EA14 QA17 AB3 EB29 | | |
| 0748 | des[B1-B2] HA8 LA14 QA17 EB3 desB30 | | |
| 0750 | des[B1-B2] HA8 EA14 QA17 AB3 EB29 | | |
| 0758 | des[B1-B2] EA8 LA14 QA17 K EB3 | | |
| 0761 | des[B1-B2] EA8 WA13 EB3 desB30 | | |
| 0762 | des[B1-B2] EA8 WA13 AB3 desB30 | | |
| 0764 | des[B1-B2] EA8 EB3 FB17 desB30 | | |
| 0766 | des[B1-B2] HA8 EB3 EB17 desB30 | | |
| 0767 | des[B1-B2] EA8 EB3 EB17 desB30 | | |
| 0768 | des[B1-B2] EA8 LA14 EB43 NB17 | | |
| 0774 | des[B1-B2] EA8 EB3 FB17 EB29 | | |
| 0780 | des[B1-B2] EA8 LA14 RA17 EB3 desB30 | | |
| 0312 | Des[B1-B3] EA8 2CI-B24 POTEE | | |
| 0626 | Des[B1-B3] EA8 EA14 QA17 desB30 | | Yes |
| 0627 | Des[B1-B3] EA8 EA14 QB13 desB30 | | |
| 0628 | Des[B1-B3] EA8 EA14 QA17 QB13 | | |
| 0629 | Des[B1-B3] HA8 EA14 QA17 desB30 | | |
| 0630 | Des[B1-B3] HA8 EA14 QB13 desB30 | | |
| 0631 | Des[B1-B3] HA8 EA14 QA17 QB13 | | |
| 0632 | Des[B1-B3] EA8 QA17 desB30 | | |
| 0633 | Des[B1-B3] EA8 EA14 QA17 EB29 | | Yes |
| 0634 | Des[B1-B3] EA8 EA14 QB13 EB29 | | |
| 0635 | Des[B1-B3] EA8 EA14 QA17 QB13 EB29 | | |
| 0636 | Des[B1-B3] HA8 EA14 QA17 EB29 | 18 | |
| 0637 | Des[B1-B3] HA8 EA14 QB13 EB29 | | |
| 0638 | Des[B1-B3] HA8 EA14 QA17 QB13 EB29 | | |
| 0639 | Des[B1-B3] EA8 QA17 EB29 | | |
| 0646 | Des[B1-B3] EA8 EA14 RA17 desB30 | | |
| 0647 | Des[B1-B3] EA8 EA14 RA17 QB13 EB22 | | |
| 0648 | Des[B1-B3] EA8 WA13 EA14 desB30 | | |
| 0650 | Des[B1-B3] HA8 WA13 EA14 desB30 | | |
| 0651 | Des[B1-B3] HA8 WA13 EA14 QB13 | | |
| 0653 | Des[B1-B3] EA8 EA14 QB13 FB17 | | |
| 0654 | Des[B1-B3] HA8 EA14 FB17 desB30 | | |
| 0655 | Des[B1-B3] HA8 EA14 QB13 FB17 | | |
| 0658 | Des[B1-B3] EA8 WA13 EA14 EB29 | | |
| 0659 | Des[B1-B3] EA8 WA13 EA14 QB13 EB29 | | |
| 0660 | Des[B1-B3] HA8 WA13 EA14 EB29 | | |
| 0661 | Des[B1-B3] HA8 WA13 EA14 QBI 3 EB29 | | |
| 0662 | Des[B1-B3] EA8 EA14 FB17 EB29 | | |
| 0663 | Des[B1-B3] EA8 EA14 QB13 FB17 EB29 | | |
| 0664 | Des[B1-B3] HA8 EA14 FB17 EB29 | | |
| 0665 | Des[B1-B3] HA8 EA14 QB13 FB17 EB29 | | |

TABLE 1-continued

Examples of Insulin Analogs of the Present Invention

| T- | Structure | Maximum blood Glucose |
|---|---|---|
| 0676 | Des[B1-B3] EA8 EA14 desB30 | |
| 0678 | Des[B1-B3] HA8 EA14 EB29 | |
| 0714 | Des[B1-B3] HA8 EA14 QA17 EB4 desB30 | |
| 0717 | Des[B1-B3] HA8 EA14 QA17 AB4 desB30 | |
| 0718 | Des[B1-B3] EA8 EA14 QA17 EB4 desB30 | |
| 0721 | Des[B1-B3] EA8 EA14 QA17 AB4 desB30 | |
| 0730 | Des[B1-B3] HA8 EA14 QA17 EB4 EB29 | |
| 0733 | Des[B1-B3] EA8 EA14 FB17 desB30 | |
| 0738 | Des[B1-B3] EA8 EA14 QA17 EB4 EB29 | |
| 0739 | Des[B1-B3] EA8 EA14 QA17 AB4 EB29 | |
| 0742 | Des[B1-B3] HA8 EA14 QA17 AB4 EB29 | |
| 0753 | Des[B1-B3] EA8 LA14 QA17 Eb4 desB30 | |
| 0754 | Des[B1-B3] HA8 LA14 QA17 EB4 desB30 | |
| 0771 | Des[B1-B3] EA8 EB4 FB17 desB30 | |
| 0772 | Des[B1-B3] HA8 EB4 EB17 desB30 | |
| 0775 | Des[B1-B3] HA8 LA14 QA17 EB4 EB29 | |

Table 2 provides a series of insulin analogues that are synthesized from plasmids in which the 5'-DNA element encoding the N-terminal pre-sequence of the single-chain precursor polypeptide contains a deletion of the codon 5' to that encoding Phe$^{B1}$. These plasmid constructs are designated "desB(minus)1" in the following entries. Those containing "KB2" (Lys$^{B2}$) enable trypsin digestion to yield a des-(B1, B2) analog whereas those containing "KB3" (Lys$^{B3}$) enable trypsin digestion to yield a des-(B1-B3) analog.

TABLE 2 desB(minus)1 insulin analogues

| T-Code | Description |
|---|---|
| 0686 | desB(minus)1 EA8 EA14 QA17 KB2 AB3 EB17 |
| 0687 | desB(minus)1 EA8 EA14 QA17 KB2 AB3 FB17 |
| 0688 | desB(minus)1 EA8 EA14 RA17 KB2 AB3 EB17 |
| 0689 | desB(minus)1 EA8 EA14 RA17 KB2 AB3 FB17 |
| 0690 | desB(minus)1 HA8 EA14 QA17 KB2 AB3 EB17 |
| 0691 | desB(minus)1 HA8 EA14 QA17 KB2 AB3 FB17 |
| 0692 | desB(minus)1 HA8 EA14 RA17 KB2 AB3 EB17 |
| 0693 | desB(minus)1 EAB EA14 QA17 KB2 EB3 EB17 |
| 0694 | desB(minus)1 EA8 EA14 QA17 KB2 EB3 FB17 |
| 0695 | desB(minus)1 EA8 EA14 RA17 KB2 EB3 EB17 |
| 0696 | desB(minus)1 EA8 EA14 RA17 KB2 EB3 FB17 |
| 0697 | desB(minus)1 HA8 EA14 QA17 KB2 EB3 EB17 |
| 0698 | desB(minus)1 HA8 EA14 QA17 KB2 EB3 FB17 |
| 099 | desB(minus)1 HA8 EA14 RA17 KB2 EB3 EB17 |
| 0700 | desB(minus)1 HA8 EA14 RA17 KB2 EB3 FB17 |

Biological activity and pharmacodynamics were tested in a subset of cases in male Sprague-Dawley rats (ca. 300 g) rendered diabetic by streptozotocin. The receptor-binding affinities of the insulin analogues were in a subset of cases determined in relation to wild-type human insulin (data not shown). Values were observed in the range 5-100% relative to wild-type human insulin in studies of the lectin-purified and detergent solubilized insulin receptor (isoforms A and B). Dissociation constants ($K_d$) were determined by fitting to a mathematic model as described by Whittaker and Whittaker (2005. *J. Biol. Chem.* 280: 20932-20936); the model employed non-linear regression with the assumption of heterologous competition (Wang, 1995, *FEBS Lett.* 360: 111-114).

A subset of insulin analogues were tested for foreshortening of the tail of insulin action following IV bolus injection into the tail vein of a STZ rat. The dose of the analogue in micrograms per 300-gram rat was adjusted relative to insulin lispro so that similar nadirs were observed (i.e., the maximal drop in blood-glucose concentration). Although in general more mass of analogue was required than mass of insulin lispro to achieve similar glycemic control, in no case was the difference more than a factor of five. Six analogues of the present invention were observed to exhibit foreshortening of the tail (defined as the area over the curve and less than the buffer control between minutes 90 and 300 relative to the total area over the curve between minutes 0 and 300). These are: des-B1, Glu$^{48}$, Gul$^{414}$, Arg$^{417}$, des-B30-insulin (T-0688), des-B1, Glu$^{B2}$, His$^{48}$, Glu$^{4144}$, Gln$^{417}$, des-B30-insulin (T-0695), des-[B1, B2], Glu$^{B3}$, His$^{48}$, Glu$^{414}$, Gln$^{417}$, des-B30-insulin-insulin (T-0706), des-B1, Ala$^{B2}$, His$^{48}$, Glu$^{414}$, Gln$^{417}$, des-B30-insulin (T-0715), des-B1, Ala$^{B2}$, Glu$^{48}$, Glu$^{414}$, Gln$^{417}$, des-B30insulin (T-0719), and des-B1, Ala$^{B2}$, Glu$^{B29}$, His$^{48}$, Glu$^{414}$, Gln$^{417}$-insulin (T-0737).

Figure 3:
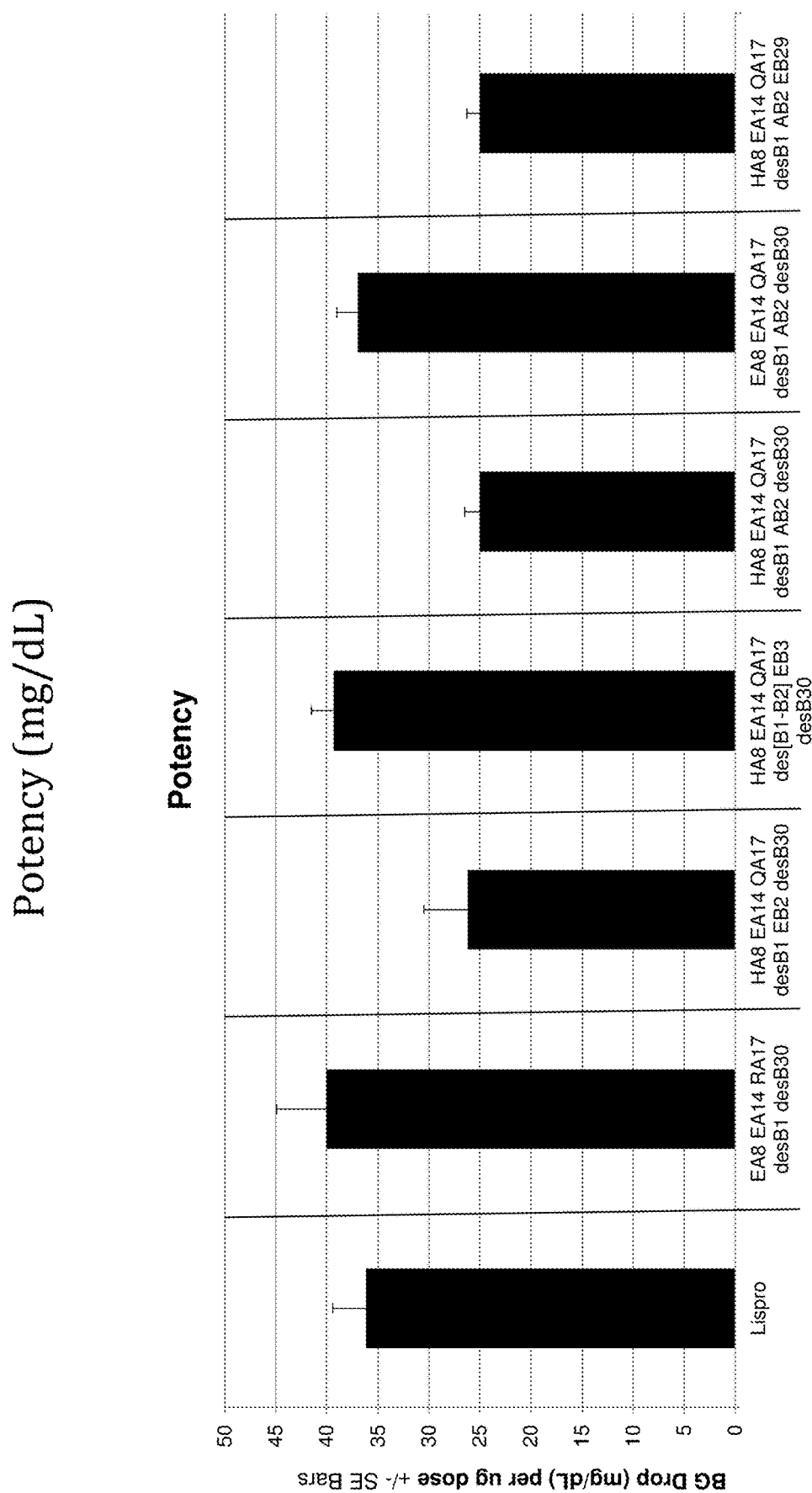
FIG. 3 is a bar graph showing the blood glucose drop (in mg/dL) per microgram of insulin analogue for several embodiments of the insulin analogue of the present invention and insulin lispro.

Potency of these analogues was evaluated in male diabetic Lewis rats. Experimental analogues, insulin lispro, and diluent only control solutions were injected subcutaneously, and the resulting changes in blood glucose (BG) were monitored by serial measurements using a clinical glucometer. Dose response was calculated as maximal BG drop in excess of the diluent control and plotted. Langmuir isotherm was fitted using iterative weighting to calculate the best-fit dose response curve and EC50 determined as the interpolated dose required to achieve a drop half way between fitted maximal and minimal drops. All experimental analogues were formulated without zinc. Results are provided in FIG. 3. Each analogue tested had a potency at least ⅔ of that of insulin lispro. Three analogues, displayed a potency equal to or greater than insulin lispro, des-B1, Glu$^{48}$, Glu$^{414}$, Arg$^{417}$, des-B30-insulin (T-0688), des-[B1, B2], Glu$^{B3}$, His$^{48}$, Glu$^{414}$, Gln$^{417}$, des-B30-insulin-insulin (T-0706), and des-B1, Ala$^{B2}$, Glu$^{48}$, Glu$^{414}$, Gln$^{417}$, des-B30insulin (T-0719).

Thermodynamic Stability. The thermodynamic stabilities of the insulin analogues were probed by CD-monitored guanidine denaturation in a subset of cases. The method was as described (Hua, Q. X., et al. *J. Biol. Chem.* 283, 14703-16 (2008)). Briefly, the change in free energies of unfolding ($\Delta G_u$) was measured by circular dichroism (CD)-detected guanidine denaturation at 25° C. at pH 7.4. The results indicate that these analogues are each as stable (and in fact more stable) to chemical denaturation than is insulin lispro (whose free energy of unfolding ($\Delta G_u$) at 25° C. is 2.9±0.1 kcal/mole). Results for selected analogues are given in Table 3 below. The estimates of $\Delta G_u$ at 25° C. provided in Table 3 were obtained by application of an analogous two-state model extrapolated to zero denaturant concentration. Such higher values of $\Delta G_u$ predict enhanced resistance of the present insulin analogues to chemical degradation under zinc-free conditions than would be observed in studies of wild-type insulin or KP-insulin under the same conditions.

Figure 4:
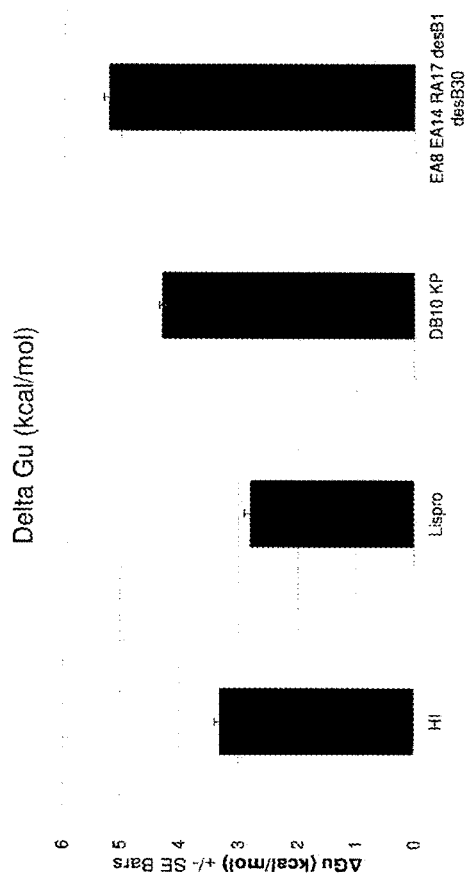
FIG. 4 is a bar graph providing a comparison of the $\Delta G_u$ values for wild type human insulin (HI); insulin lispro (lispro); AspB10-insulin lispro (DB10, KP); and EAB, EA14, RA17 des B1, des B30 insulin (T-0688).

A graphic presentation of change in free energies of unfolding values for a similar comparison of human insulin (HI), insulin lispro (lispro), AspB10-KP insulin (DB10 KP), and EA8 EA14 RA17 des B1 des B30 insulin according to the invention is provided in FIG. 4. The change in free energies of unfolding ($\Delta G_u$) was measured by circular dichroism (CD)-detected guanidine denaturation at 25° C. at pH 7.4. The experimental analogues were formulated without zinc. The augmentation in stability is at least 1 kcal/mole, achieving a value of $\Delta G_u$ similar or greater than that of $Asp^B10$-insulin, an analogue known in the art to possess sufficient stability to enable effective zinc-free formulation. These data demonstrate that a zinc-free insulin analog may be made as stable as AspB10-insulin without use of an unnatural amino-acid substitution and with the native Histidine at position B10.

TABLE 3

Thermodynamic Stabilities of Selected Insulin Analogues

| T- code | Structure | $\Delta Gu$ (kcal/mol) | S.D. | Cmid | S.D. |
| --- | --- | --- | --- | --- | --- |
| T-0636 | HA8 EA14 QA17 des[B1-B3] EB29 | 4.4 | 0.1 | 5.4 | 0.2 |
| T-0674 | HA8 EA14 desB1 desB30 | 5 | 0.2 | 5.8 | 0.3 |
| T-0675 | HA8 EA14 des[B1-B2] desB30 | 4.8 | 0.2 | 5.5 | 0.1 |
| T-0680 | EA8 EA14 QA17 desB1 desB30 | 5.1 | 0.2 | 5.5 | 0.2 |
| T-0681 | EA8 EA14 QA17 desB1 EB29 | 4.5 | 0.1 | 5.9 | 0.1 |
| T-0688 | EA8 EA14 RA17 desB1 desB30 | 5.2 | 0.1 | 5.8 | 0.2 |
| T-0690 | EA8 EA14 RA17 des[B1-B2] QB13 EB22 desB30 | 5 | 0.1 | 5.9 | 0.2 |
| T-0694 | HA8 EA14 RA17 desB1 EB22 desB30 | 5.3 | 0.1 | 6 | 0.1 |

Figure 5:
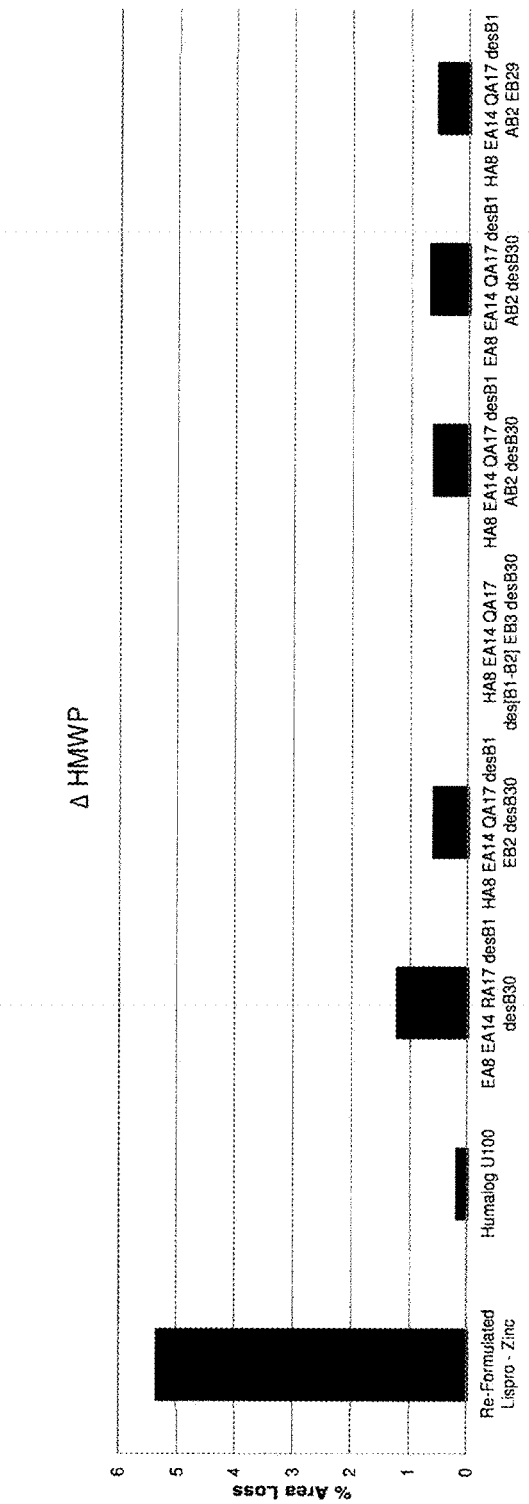
FIG. 5 is a bar graph providing the change in percentage of high molecular weight protein (HMWP) of embodiments of the insulin analogue of the present invention at 45° C. for 7 days as determined by reverse-phase HPLC. All experimental samples were formulated without zinc.

Physical Stability—High Molecular Weight Protein Formation. The stability of analogues of the claimed invention were also tested for stability by analysis of formation of high molecular weight proteins. Nominal U-100 formulations of several insulin analogues were heat stressed at 45° C. for 7 days and assayed for formation of high molecular weight proteins (HMWP) by reverse-phase HPLC. FIG. 5 shows changes in percentage of HMWP from day 1 to day 7 for analogues: des-B1, $Glu^{A8}$, $Glu^{A14}$, $Arg^{A17}$, des-B30-insulin (T-0688), des-B1, $Glu^{B2}$, $His^{A8}$, $Glu^{A14}$, $Gln^{A17}$, des-B30-insulin (T-0695), des-[B1, B2], $Glu^{B3}$, $His^{A8}$, $Glu^{A14}$, $Gln^{A17}$, des-B30-insulin-insulin (T-0706), des-B1, $Ala^{B2}$, $His^{A8}$, $Glu^{A14}$, $Gln^{A17}$, des-B30-insulin (T-0715), des-B1, $Ala^{B2}$, $Glu^{A8}$, $Glu^{A14}$, $Gln^{A17}$, des-B30insulin (T-0719), and des-B1, $Ala^{B2}$, $Glu^{B29}$, $His^{A8}$, $Glu^{A14}$, $Gln^{A17}$-insulin (T-0737). All experimental analogues were formulated without zinc. A 2 percent area loss or greater (for the elution profile for the insulin analogue) was considered a failure. Each of the analogues of the claimed invention exhibited less than 2 percent area loss, and actually less than 1.5 percent area loss. Four of the five analogues tested, T-0695, T-0706, T-0715, T-0719, T-0737, all exhibited less than 1 percent area loss. In this way, the insulin analogues tested that were formulated without zinc were closer in behavior to standard Humalog® U100 (insulin lispro; Eli Lilly) than to insulin lispro reformulated in a zinc-free solution.

Assessment of Fibril Formation. Insulin lispro or embodiments of the insulin analogues of the claimed invention were made 60 μM in phosphate-buffered saline (pH 7.4) containing 0.1% sodium azide and gently rocked at 37° C. in glass vials in the presence of a liquid/air interface. Aliquots were taken at regular intervals and frozen for later analysis of thioflavin T (ThT) fluorescence. The assay was terminated on visual appearance of cloudiness. Five analogues are thus tested for prolongation of the lag time prior to onset of ThT-positive fibrillation: des-B1, $Glu^{A8}$, $Glu^{A14}$, $Arg^{A17}$ des-B30-insulin (T-0688), des-B1, $Glu^{B2}$, $His^{A}s$, $Glu^{A14}$, $Gln^{A17}$, des-B30-insulin (T-0695), des-[B1, B2], $Glu^{B3}$, $His^{A8}$, $Glu^{A14}$, $Gln^{A17}$, des-B30-insulin-insulin (T-0706), des-B1, $Ala^{B2}$, $His^{A8}$, $Glu^{A14}$, $Gln^{A17}$, des-B30-insulin (T-0715), and des-B1, $Ala^{B2}$, $Glu^{B29}$, $His^{A8}$, $Glu^{A14}$, $Gln^{A17}$-insulin (T-0737). Whereas on multiple testing insulin lispro exhibited lag times of 2-4 days under these conditions, the lag times of each of the analogues tested was prolonged by a factor of at least tenfold.

Figure 6:
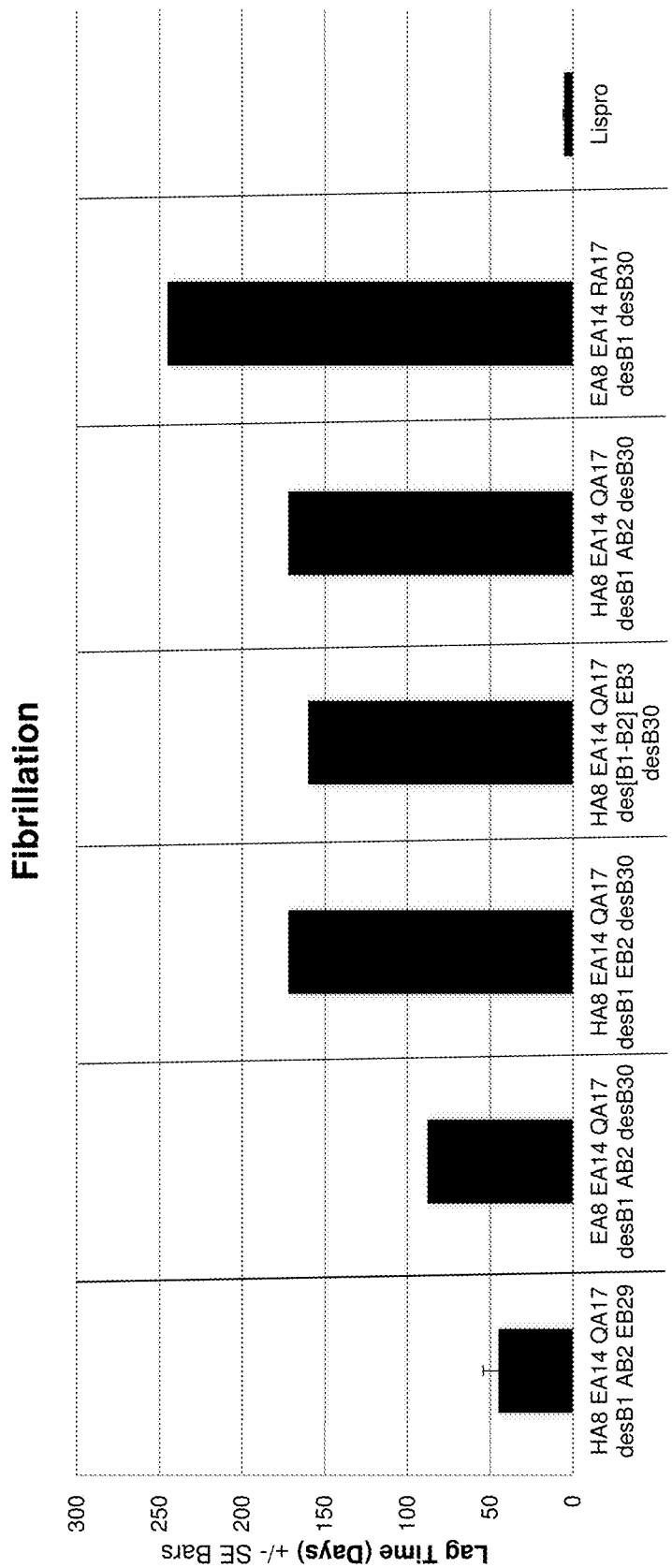
FIG. 6 is a bar graph providing the fibrillation lag time of embodiments of the insulin analogue of the present invention and that of insulin lispro in phosphate buffered saline (PBS), pH 7.4 at 40° C. with a constant shake of 1000 cpm. All experimental samples were formulated without zinc.

A similar assay was also performed. Insulin lispro or embodiments of the insulin analogues of the claimed invention were formulated to a final concentration of U10 in phosphate-buffered saline (PBS, pH 7.4) containing 0.1% sodium azide and without zinc and gently rocked at 37° C. in glass vials in the presence of a liquid/air interface. 1 μM thio Flavin T (ThT) was added to each solution and 150 μl was added to each well. The plate was incubated at 40° C. with a constant linear shake of 1000 cpm. Analysis of thioflavin T (ThT) fluorescence by excitation/emission wavelengths of 440/480 nm. FIG. 6 is a graph comparing the fibrillation lag time of these insulin analogues and insulin lispro. The samples tested were: des-B1, $Glu^{A8}$, $Glu^{A14}$, $Arg^{A17}$, des-B30-insulin (T-0688), des-B1, $Glu^{B2}$, $His^{A8}$, $Glu^{A14}$, $Gln^{A17}$, des-B30-insulin (T-0695), des-[B1, B2], $Glu^{B3}$, $His^{A8}$, $Glu^{A14}$, $Gln^{A17}$, des-B30-insulin-insulin (T-0706), des-B1, $Ala^{B2}$, $His^{A8}$, $Glu^{A14}$, $Gln^{A17}$, des-B30-insulin (T-0715), des-B1, $Ala^{B2}$, $Glu^{B29}$, $His^{A8}$, $Glu^{A14}$, $Gln^{A17}$-insulin (T-0737) and des-B1, $Glu^{A8}$, $Glu^{A14}$, $Gln^{A17}$, $Ala^{B2}$, des-B30-insulin (T-0719).

Figure 7:
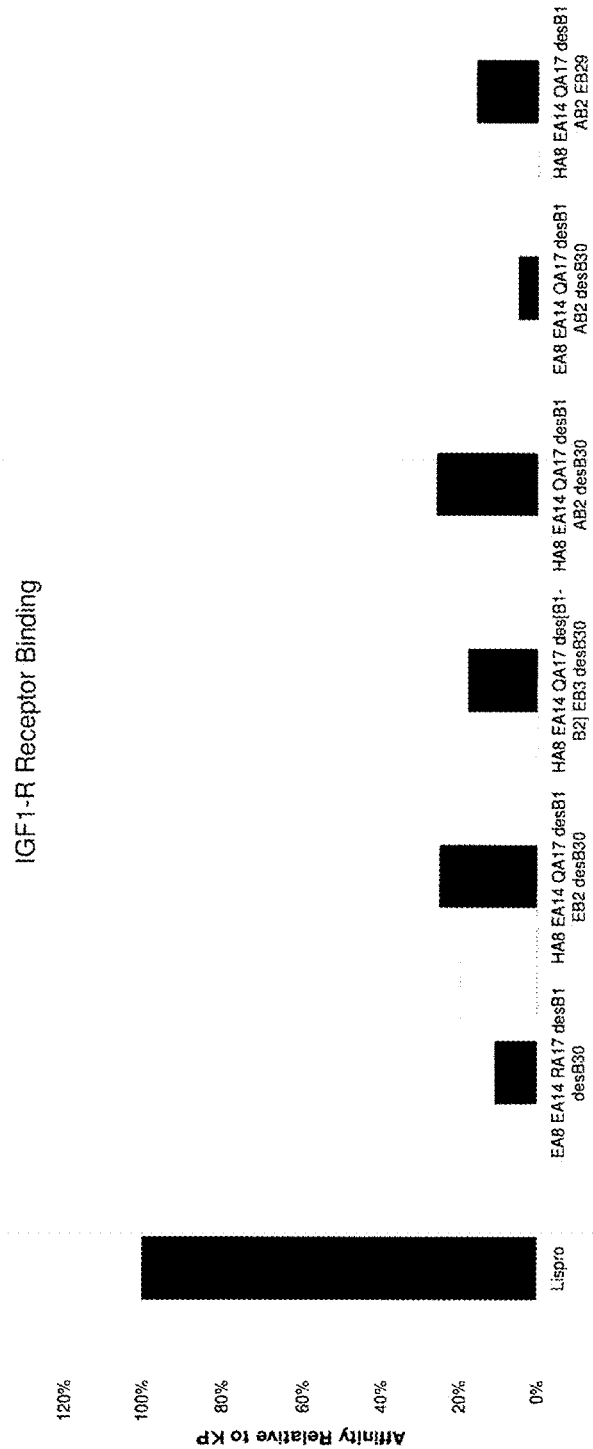
FIG. 7 is a bar graph providing the binding affinity of embodiments of the insulin analogue of the present invention to human type 1 insulin-like growth factor receptor (hIGFR) relative to insulin lispro. Relative affinity is defined as the ratio of dissociation constants as determined by competitive displacement of bound $^{125}$I-labeled human insulin. All experimental samples were formulated without zinc.

IGF-R Binding Affinity. As stated above, reduced binding to the mitogenic Type 1 IGF receptor (IGF-R1) would be advantageous. Table 4 and FIG. 7 provide the binding affinity of several embodiments of the insulin analogue of the claimed invention relative to insulin lispro. The samples tested were: des-B1, $Glu^{A8}$, $Glu^{A14}$, $Arg^{A17}$, des-B30-insulin (T-0688), des-B1, $Glu^{B2}$, $His^{A8}$, $Glu^{A14}$, $Gln^{A17}$, des-B30-insulin (T-0695), des-[B1, B2], $Glu^{B3}$, $His^{A8}$, $Glu^{A14}$, $Gln^{A17}$, des-B30-insulin-insulin (T-0706), des-B1, $Ala^{B2}$, $His^{A8}$, $Glu^{A14}$, $Gln^{A17}$, des-B30-insulin (T-0715), des-B1, $Ala^{B2}$, $Glu^{B29}$, $His^{A8}$, $Glu^{A14}$, $Gln^{A17}$-insulin (T-0737) and des-B1, $Glu^{A8}$, $Glu^{A14}$, $Gln^{A17}$, $Ala^{B2}$, des-B30-insulin (T-0719). Studies employed a FLAG epitope-tagged holoreceptor to human type 1 insulin-like growth factor receptor (hIGFR) bound to 96 well plates coated with anti-FLAG monoclonal antibody. Relative affinity is defined as the ratio of dissociation constants as determined by competitive displacement of bound $^{125}I$ labeled human insulin. All experimental analogues were formulated without zinc. Each embodiment of the claimed invention tested here displayed 26 percent or less of the affinity for IGF-R than insulin lispro. Four analogues, T-0688, T-0706, T-0719, and T-0737, displayed less than 20 percent of the affinity of insulin lispro for IGF-R1. One analogue, T-0719, displayed less than 10 percent of the binding affinity of insulin lispro for IGF-R1

TABLE 4

Relative IGF-R1 Binding Affinity

| T-Code | Sequence Description | IGF1-R (Rel. Aff.) ≤HI/KP | kD | Binding Affinity |
|---|---|---|---|---|
| Lispro | Lispro | 100% | | |
| T-0688 | EA8 EA14 RA17 desB1 desB30 | 11% | 6.72 | 0.15 |
| T-0695 | HA8 EA14 QA17 desB1 EB2 desB30 | 25% | 4.33 | 0.23 |
| T-0706 | HA8 EA14 QA17 des[B1-B2] EB3 desB30 | 18% | 6.09 | 0.16 |
| T-0715 | HA8 EA14 QA17 desB1 AB2 desB30 | 26% | 4.16 | 0.24 |
| T-0719 | EA8 EA14 QA17 desB1 AB2 desB30 | 5% | 38.04 | 0.03 |
| T-0737 | HA8 EA14 QA17 desB1 AB2 EB29 | 16% | 12.52 | 0.08 |

Figure 8:
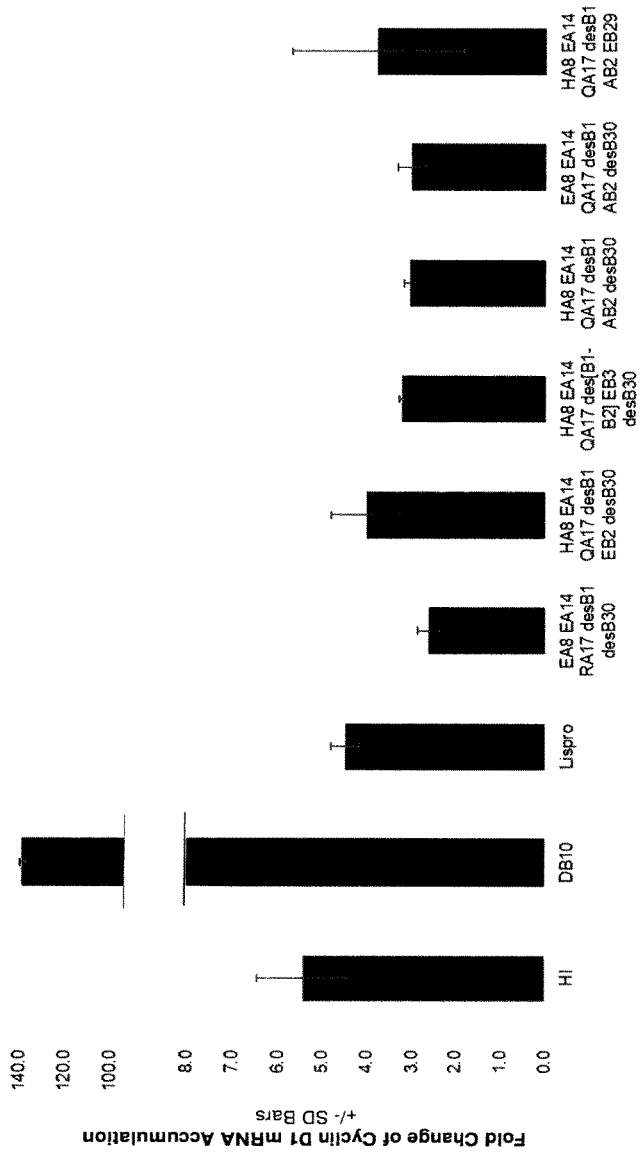
FIG. 8 is a bar graph providing the change in Cyclin D1 mRNA accumulation utilizing a rat myoblast cell line (L6) with high expression of insulin receptor as the cell model. All experimental samples were formulated without zinc.

Mitogenicity—Cyclin regulation. RT-qPCR assay monitored the transcription responses of mitogenicity probes stimulated by treatment of different insulin analogues. Expression regulation of two cyclins served as major probes. Cyclin D1 up-regulation and cyclin G2 down-regulation correlates to the active cell division cycle (proliferation, which is generally correlated to mitogenicity). A ratio of D1/G2 transcription levels gives a picture of the mitogenic potential of a compound; a higher ratio means more mitogenic potential. In this assay, a rat myoblast cell line (L6) with high-expression of insulin receptor (IR) served as the cell model. All experimental analogues were formulated without zinc. The samples tested were: des-B1, $Glu^{48}$, $Glu^{414}$, $Arg^{417}$, des-B30-insulin (T-0688), des-B1, $Glu^{B2}$, $His^{48}$, $Glu^{414}$, $Gln^{417}$, des-B30-insulin (T-0695), des-[B1, B2], $Glu^{B3}$, $His^{48}$, $Glu^{414}$, $Gln^{417}$, des-B30-insulin-insulin (T-0706), des-B1, $Ala^{B2}$, $His^{48}$, $Glu^{414}$, $Gln^{417}$, des-B30-insulin (T-0715), des-B1, $Ala^{B2}$, $Glu^{B29}$, $His^{48}$, $Glu^{414}$, $Gln^{417}$-insulin (T-0737) and des-B1, $Glu^{48}$, $Glu^{414}$, $Gln^{417}$, $Ala^{B2}$, des-B30-insulin (T-0719). The mRNA accumulation for Cyclin D1 and Cyclin G2, and the ratio of Cyclin D1/Cyclin G2, with their standard deviations, are provided in Table 5. The change in Cyclin D1 mRNA accumulation is provided in FIG. 8. Each of the embodiments of the claimed invention tested possessed a Cyclin D1/Cyclin G2 ratio less than that of both human insulin and insulin lispro.

TABLE 5

Cyclin D1 and Cyclin G Expression

| T-Code | Sequence | D1 | SD D1 | G2 | SD G2 | Cyclin D1/G2 |
|---|---|---|---|---|---|---|
| HI | HI | 5.5 | 1.0 | 0.29 | 0.04 | 18.8 |
| DB10 | DB10 | 18.0 | 1.2 | 0.13 | 0.01 | 138.8 |
| Lispro | Lispro | 4.5 | 0.3 | 0.36 | 0.03 | 12.4 |
| T-0688 | EA8 EA14 RA17 desB1 desB30 | 2.6 | 0.3 | 0.49 | 0.07 | 5.4 |
| T-0695 | HA8 EA14 QA17 desB1 EB2 desB30 | 4.0 | 0.8 | 0.34 | 0.06 | 11.8 |
| T-0706 | HA8 EA14 QA17 des[B1-B2] EB3 desB30 | 3.3 | 0.1 | 0.40 | 0.13 | 8.1 |
| T-0715 | HA8 EA14 QA17 desB1 AB2 desB30 | 3.1 | 0.1 | 0.45 | 0.03 | 6.8 |
| T-0719 | EA8 EA14 QA17 desB1 AB2 desB30 | 3.0 | 0.3 | 0.47 | 0.03 | 6.5 |
| T-0737 | HA8 EA14 QA17 desB1 AB2 EB29 | 3.8 | 1.9 | 0.48 | 0.30 | 7.9 |

Since most of these analogues also exhibited a foreshortened tail on IV bolus injection in STZ rats (above), these data together demonstrate that tradeoffs can in principle be circumvented to obtain combinations of modifications to achieve the desired therapeutic and pharmacologic properties.

We envision the analogues of the present invention providing a method for the treatment of diabetes mellitus or the metabolic syndrome. The route of delivery of the insulin analogue is by subcutaneous injection through the use of a syringe or pen device. An insulin analogue of the present invention may also contain a foreshortened B-chain due to deletion of residues B1, B1-B2, B1-B3 and/or B30. Insulin analogues of the present invention may also contain B chains extended by one- or two residues (formal positions B31 and B32), at least one of which is an acidic residue (Aspartic Acid or Glutamic Acid).

A pharmaceutical composition may comprise such insulin analogues in a formulation that specifically excludes zinc ions or other divalent metal ions to avoid formation of metal-ion-stabilized insulin analogue hexamers. The pH of the formulation is in the range pH 7.0-8.0; a buffer (typically sodium phosphate or Tris-hydrochloride) may or may not be present. In such a formulation, the concentration of the insulin analogue would typically be in the range 0.6-6.0 mM; concentrations up to 6 mM may be used in vial or pen; the more concentrated formulations (U-200 or higher) may be of particular benefit in patients with marked insulin resistance. Excipients may include agents intended to accelerate absorption of the hormone from the subcutaneous depot into the bloodstream (such as sodium EDTA or sodium EGTA, arginine, and nicotinamide), glycerol, glycine, Tris-hydrochloride or other buffers, sodium chloride or other salts, and anti-microbial preservatives such as phenol and/or meta-cresol. Such a pharmaceutical composition may be used to treat a patient having diabetes mellitus or other medical condition by administering a physiologically effective amount of the composition to the patient.

Based upon the foregoing disclosure, it should now be apparent that the two-chain insulin analogues provided will carry out the objects set forth hereinabove. Namely, these insulin analogues exhibit biological activity (as defined by the nanomoles of protein monomer required to lower the blood-glucose concentration in a mammal on subcutaneous or intravenous injection) similar to that of wild-type insulin but with sufficient intrinsic stability to enable formulation in the absence of zinc ions (or other divalent metal ions) at protein concentrations in the range 0.6-6.0 mM. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Brange J, editor. (1987) *Galenics of Insulin: The Physicochemical and Pharmaceutical Aspects of Insulin and Insulin Preparations.* Berlin: Springer Berlin Heidelberg.

Liu, M., Hua, Q. X., Hu, S. Q., Jia, W., Yang, Y., Saith, S. E., Whittaker, J., Arvan, P., and Weiss, M. A. (2010) Deciphering the hidden informational content of protein sequences: foldability of proinsulin hinges on a flexible arm that is dispensable in the mature hormone. *J. Biol. Chem.* 285:30989-1001.

Vølund, A., Brange, J., Drejer, K., Jensen, I., Markussen, J., Ribel, U., Sørensen, A. R., and Schlichtkrull, J. (1991) In vitro and in vivo potency of insulin analogues designed for clinical use. *Diabet. Med.* 8:839-47.

Wang, Z. X. (1995) An exact mathematical expression for describing competitive binding of two different ligands to a protein molecule *FEBS Lett.* 360: 111-114.

Whittaker, J., and Whittaker, L. (2005) Characterization of the functional insulin binding epitopes of the full-length insulin receptor. *J. Biol. Chem.* 280: 20932-20936.

Yang, Y., Petkova, A., Huang, K., Xu, B., Hua, Q. X., Ye, I. J., Chu, Y. C., Hu, S. Q., Phillips, N. B., Whittaker, J., Ismail-Beigi, F., Mackin, R. B., Katsoyannis, P. G., Tycko, R., and Weiss, M. A. (2010) An Achilles' heel in an amyloidogenic protein and its repair: insulin fibrillation and therapeutic design. *J. Biol. Chem.* 285:10806-21.

---

What is claimed is:

1. An insulin analogue comprising a modified A-chain polypeptide and a modified B-chain polypeptide, wherein the modified A-chain polypeptide comprises the amino acid sequence of SEQ ID NO: 2, with a Glu substitution at position A8 and a Glu substitution at position A14 relative to SEQ ID NO: 2, and further wherein the modified A-chain polypeptide further comprises one or more substitutions relative to SEQ ID NO: 2 selected from the group consisting of:
   a substitution at position A17 selected from the group consisting of a Gln, Ala, His, Leu, Phe, Tyr and Arg substitution; and
   a substitution at position A21 selected from the group consisting of an Ala, Gly and Glu substitution;
and wherein the modified B-chain polypeptide comprises the amino acid sequence of SEQ ID NO: 3, with a deletion of the amino acid at position B1, an Ala substitution at position B2 and a Glu substitution at position B3, relative to SEQ ID NO: 3, and further wherein the modified B-chain polypeptide further comprises one or more modifications relative to SEQ ID NO: 3 selected from the group consisting of:
   a substitution at position B28 selected from the group consisting of an Ala, Arg, Glu and Lys substitution at B28;
   a substitution at position B29 selected from the group consisting of an Ala, Arg, Pro and Glu substitution at B29.

2. The insulin analogue of claim 1, wherein the modified A-chain polypeptide additionally comprises a Gln substitution at position A17.

3. The insulin analogue of claim 1, wherein the modified A-chain polypeptide additionally comprises a Arg substitution at position A17.

4. The insulin analogue of claim 1, wherein the modified B-chain polypeptide additionally comprises a deletion of the amino acid at position B30.

5. The insulin analogue of claim 1, comprising a Glu substitution at position B29.

6. A method of lowering the blood sugar of a patient, the method comprising administering a physiologically effective amount of an insulin analogue or a physiologically acceptable salt thereof to the patient, wherein the insulin analogue comprises a modified A-chain polypeptide and a modified B-chain polypeptide, wherein the modified A-chain polypeptide comprises the amino acid sequence of SEQ ID NO: 2, with a Glu substitution at position A8 and a Glu substitution at position A14 relative to SEQ ID NO: 2, and further wherein the modified A-chain polypeptide further comprises one or more substitutions relative to SEQ ID NO: 2 selected from the group consisting of:
 a substitution at position A17 selected from the group consisting of a Gln, Ala, His, Leu, Phe, Tyr and Arg substitution; and
 a substitution at position A21 selected from the group consisting of an Ala, Gly and Glu substitution;
and wherein the modified B-chain polypeptide comprises the amino acid sequence of SEQ ID NO: 3, with a deletion of the amino acid at position B1, an Ala substitution is present at position B2 and a Glu substitution at position B3, relative to SEQ ID NO: 3, and further wherein the modified B-chain polypeptide further comprises one or more modifications relative to SEQ ID NO: 3 selected from the group consisting of:
 a substitution at position B28 selected from the group consisting of an Ala, Arg, Glu and Lys;
 a substitution at position B29 selected from the group consisting of an Ala, Arg, Pro and Glu.

7. The method of claim 6, wherein the modified A-chain polypeptide additionally comprises a Gln substitution at position A17.

8. The method of claim 6, wherein the modified A-chain polypeptide additionally comprises a Arg substitution at position A17.

9. The method of claim 6, wherein the modified B-chain polypeptide additionally comprises a deletion of the amino acid at position B30.

10. The method of claim 6, wherein the modified B-chain polypeptide additionally comprises a Glu substitution at position B29.

* * * * *

SEQUENCE LISTING

```
<160> NUMBER OF SEQ ID NOS: 111

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 21
<212> TYPE: PRT
<213> ORGANISM: Artificial Sequence
<220> FEATURE:
```

```
<223> OTHER INFORMATION: insulin analogue
<220> FEATURE:
<221> NAME/KEY: MISC_FEATURE
<222> LOCATION: (8)..(8)
<223> OTHER INFORMATION: X may be Thr, His, Glu, Ala, Met, Gly, Ser,
      Asp, Lys or Arg
<220> FEATURE:
<221> NAME/KEY: MISC_FEATURE
<222> LOCATION: (12)..(12)
<223> OTHER INFORMATION: X may be Ser, Ala, Asp, Glu or His
<220> FEATURE:
<221> NAME/KEY: MISC_FEATURE
<222> LOCATION: (13)..(13)
<223> OTHER INFORMATION: X may be Leu, Ala, Glu, His, Phe, Tyr or Trp
<220> FEATURE:
<221> NAME/KEY: MISC_FEATURE
<222> LOCATION: (14)..(14)
<223> OTHER INFORMATION: X may be Tyr, Ala, Glu, Gln, His or Leu
<220> FEATURE:
<221> NAME/KEY: MISC_FEATURE
<222> LOCATION: (17)..(17)
<223> OTHER INFORMATION: X may be Glu, Ala, Arg, Gln, His, Leu, Phe or
      Tyr
<220> FEATURE:
<221> NAME/KEY: MISC_FEATURE
<222> LOCATION: (21)..(21)
<223> OTHER INFORMATION: X may be Asn, Ala, Gly or Glu

<400> SEQUENCE: 4

Gly Ile Val Glu Gln Cys Cys Xaa Ser Ile Cys Xaa Xaa Xaa Gln Leu
1               5                   10                  15

Xaa Asn Tyr Cys Xaa
            20

<210> SEQ ID NO 5
<211> LENGTH: 32
<212> TYPE: PRT
<213> ORGANISM: Artificial Sequence
<220> FEATURE:
<223> OTHER INFORMATION: insulin analogue
<220> FEATURE:
<221> NAME/KEY: MISC_FEATURE
<222> LOCATION: (1)..(3)
<223> OTHER INFORMATION: X may be Phe-Val-Asn or Ala-Asn, Glu-Asn,
      Ala-Ala, Ala-Glu, Glu-Glu, Asn-Glu, Asn-Ala, Glu-Ala, Ala-His, or
      Glu-His
<220> FEATURE:
<221> NAME/KEY: MISC_FEATURE
<222> LOCATION: (4)..(4)
<223> OTHER INFORMATION: X may be Gln, Ala or Glu
<220> FEATURE:
<221> NAME/KEY: MISC_FEATURE
<222> LOCATION: (13)..(13)
<223> OTHER INFORMATION: X may be Glu, Ala, Gln, His or Leu
<220> FEATURE:
<221> NAME/KEY: MISC_FEATURE
<222> LOCATION: (17)..(17)
<223> OTHER INFORMATION: X may be Leu, Ala, Arg, Glu, His, Lys, Phe,
      Trp, Tyr or Val
<220> FEATURE:
<221> NAME/KEY: MISC_FEATURE
<222> LOCATION: (18)..(18)
<223> OTHER INFORMATION: X may be Val, Ala, His, Leu, Lys, Glu, Phe,
      Thr, Trp or Tyr
<220> FEATURE:
<221> NAME/KEY: MISC_FEATURE
<222> LOCATION: (28)..(28)
<223> OTHER INFORMATION: X may be Pro, Ala, Arg, Glu, or Lys
<220> FEATURE:
<221> NAME/KEY: MISC_FEATURE
<222> LOCATION: (29)..(29)
<223> OTHER INFORMATION: X may be Lys, Ala, Arg, Glu, or Pro
<220> FEATURE:
<221> NAME/KEY: MISC_FEATURE
<222> LOCATION: (30)..(30)
<223> OTHER INFORMATION: X may be Thr or may be absent
```

```
<220> FEATURE:
<221> NAME/KEY: MISC_FEATURE
<222> LOCATION: (31)..(32)
<223> OTHER INFORMATION: X is one or two amino acids, one of which is
      Asp or Glu, or is absent

<400> SEQUENCE: 5

Xaa Xaa Xaa Xaa His Leu Cys Gly Ser His Leu Ala Xaa Ala Leu Tyr
1               5                   10                  15

Xaa Xaa Cys Gly Glu Arg Gly Phe Phe Tyr Thr Xaa Xaa Xaa Xaa Xaa
            20                  25                  30

<210> SEQ ID NO 6
<211> LENGTH: 29
<212> TYPE: PRT
<213> ORGANISM: Artificial Sequence
<220> FEATURE:
<223> OTHER INFORMATION: des-(B1) derivative of GluB28-insulin

<400> SEQUENCE: 6

Val Asn Gln His Leu Cys Gly Ser His Leu Val Glu Ala Leu Tyr Leu
1               5                   10                  15

Val Cys Gly Glu Arg Gly Phe Phe Tyr Thr Glu Lys Thr
            20                  25

<210> SEQ ID NO 7
<211> LENGTH: 28
<212> TYPE: PRT
<213> ORGANISM: Artificial Sequence
<220> FEATURE:
<223> OTHER INFORMATION: des (B1, B2) derivative of GluB28 insulin

<400> SEQUENCE: 7

Asn Gln His Leu Cys Gly Ser His Leu Val Glu Ala Leu Tyr Leu Val
1               5                   10                  15

Cys Gly Glu Arg Gly Phe Phe Tyr Thr Glu Lys Thr
            20                  25

<210> SEQ ID NO 8
<211> LENGTH: 27
<212> TYPE: PRT
<213> ORGANISM: Artificial Sequence
<220> FEATURE:
<223> OTHER INFORMATION: des (B1 B3) derivative of GluB28 insulin

<400> SEQUENCE: 8

Gln His Leu Cys Gly Ser His Leu Val Glu Ala Leu Tyr Leu Val Cys
1               5                   10                  15

Gly Glu Arg Gly Phe Phe Tyr Thr Glu Lys Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: des (B1) derivative of AspB28 insulin

<400> SEQUENCE: 9

Val Asn Gln His Leu Cys Gly Ser His Leu Val Glu Ala Leu Tyr Leu
1               5                   10                  15

Val Cys Gly Glu Arg Gly Phe Phe Tyr Thr Asp Lys Thr
            20                  25
```

```
<210> SEQ ID NO 10
<211> LENGTH: 28
<212> TYPE: PRT
<213> ORGANISM: Artificial Sequence
<220> FEATURE:
<223> OTHER INFORMATION: des (B1, B2) derivative of AspB28 insulin

<400> SEQUENCE: 10

Asn Gln His Leu Cys Gly Ser His Leu Val Glu Ala Leu Tyr Leu Val
1               5                   10                  15

Cys Gly Glu Arg Gly Phe Phe Tyr Thr Asp Lys Thr
            20                  25

<210> SEQ ID NO 11
<211> LENGTH: 27
<212> TYPE: PRT
<213> ORGANISM: Artificial Sequence
<220> FEATURE:
<223> OTHER INFORMATION: des (B1 B3) derivative of AspB28 insulin

<400> SEQUENCE: 11

Gln His Leu Cys Gly Ser His Leu Val Glu Ala Leu Tyr Leu Val Cys
1               5                   10                  15

Gly Glu Arg Gly Phe Phe Tyr Thr Asp Lys Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: des (B1) derivative of (LysB28, ProB29) insulin

<400> SEQUENCE: 12

Val Asn Gln His Leu Cys Gly Ser His Leu Val Glu Ala Leu Tyr Leu
1               5                   10                  15

Val Cys Gly Glu Arg Gly Phe Phe Tyr Thr Lys Pro Thr
            20                  25

<210> SEQ ID NO 13
<211> LENGTH: 28
<212> TYPE: PRT
<213> ORGANISM: Artificial Sequence
<220> FEATURE:
<223> OTHER INFORMATION: des (B1, B2) derivative of (LysB28, ProB29)
      insulin

<400> SEQUENCE: 13

Asn Gln His Leu Cys Gly Ser His Leu Val Glu Ala Leu Tyr Leu Val
1               5                   10                  15

Cys Gly Glu Arg Gly Phe Phe Tyr Thr Lys Pro Thr
            20                  25

<210> SEQ ID NO 14
<211> LENGTH: 27
<212> TYPE: PRT
<213> ORGANISM: Artificial Sequence
<220> FEATURE:
<223> OTHER INFORMATION: des (B1 B3) derivative of (LysB28, ProB29)
      insulin

<400> SEQUENCE: 14

Gln His Leu Cys Gly Ser His Leu Val Glu Ala Leu Tyr Leu Val Cys
1               5                   10                  15

Gly Glu Arg Gly Phe Phe Tyr Thr Lys Pro Thr
```

20                  25

<210> SEQ ID NO 15
<211> LENGTH: 29
<212> TYPE: PRT
<213> ORGANISM: Artificial Sequence
<220> FEATURE:
<223> OTHER INFORMATION: des (B1) derivative of (Ala B28) insulin

<400> SEQUENCE: 15

Val Asn Gln His Leu Cys Gly Ser His Leu Val Glu Ala Leu Tyr Leu
1               5                   10                  15

Val Cys Gly Glu Arg Gly Phe Phe Tyr Thr Ala Lys Thr
            20                  25

<210> SEQ ID NO 16
<211> LENGTH: 28
<212> TYPE: PRT
<213> ORGANISM: Artificial Sequence
<220> FEATURE:
<223> OTHER INFORMATION: des (B1, B2) derivative of (AlaB28) insulin

<400> SEQUENCE: 16

Asn Gln His Leu Cys Gly Ser His Leu Val Glu Ala Leu Tyr Leu Val
1               5                   10                  15

Cys Gly Glu Arg Gly Phe Phe Tyr Thr Ala Lys Thr
            20                  25

<210> SEQ ID NO 17
<211> LENGTH: 27
<212> TYPE: PRT
<213> ORGANISM: Artificial Sequence
<220> FEATURE:
<223> OTHER INFORMATION: des (B1 B3) derivative of (AlaB28) insulin

<400> SEQUENCE: 17

Gln His Leu Cys Gly Ser His Leu Val Glu Ala Leu Tyr Leu Val Cys
1               5                   10                  15

Gly Glu Arg Gly Phe Phe Tyr Thr Ala Lys Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: des (B1) derivative of (GluB28, ProB29) insulin

<400> SEQUENCE: 18

Val Asn Gln His Leu Cys Gly Ser His Leu Val Glu Ala Leu Tyr Leu
1               5                   10                  15

Val Cys Gly Glu Arg Gly Phe Phe Tyr Thr Glu Pro Thr
            20                  25

<210> SEQ ID NO 19
<211> LENGTH: 28
<212> TYPE: PRT
<213> ORGANISM: Artificial Sequence
<220> FEATURE:
<223> OTHER INFORMATION: des (B1, B2) derivative of (GluB28, ProB29)
      insulin

<400> SEQUENCE: 19

Asn Gln His Leu Cys Gly Ser His Leu Val Glu Ala Leu Tyr Leu Val
1               5                   10                  15

Cys Gly Glu Arg Gly Phe Phe Tyr Thr Glu Pro Thr
            20                  25

<210> SEQ ID NO 20
<211> LENGTH: 27
<212> TYPE: PRT
<213> ORGANISM: Artificial Sequence
<220> FEATURE:
<223> OTHER INFORMATION: des (B1 B3) derivative of (GluB28, ProB29)
      insulin

<400> SEQUENCE: 20

Gln His Leu Cys Gly Ser His Leu Val Glu Ala Leu Tyr Leu Val Cys
1               5                   10                  15

Gly Glu Arg Gly Phe Phe Tyr Thr Glu Pro Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: des (B1) derivative of (AlaB28, ProB29) insulin

<400> SEQUENCE: 21

Val Asn Gln His Leu Cys Gly Ser His Leu Val Glu Ala Leu Tyr Leu
1               5                   10                  15

Val Cys Gly Glu Arg Gly Phe Phe Tyr Thr Ala Pro Thr
            20                  25

<210> SEQ ID NO 22
<211> LENGTH: 28
<212> TYPE: PRT
<213> ORGANISM: Artificial Sequence
<220> FEATURE:
<223> OTHER INFORMATION: des (B1, B2) derivative of (AlaB28, ProB29)
      insulin

<400> SEQUENCE: 22

Asn Gln His Leu Cys Gly Ser His Leu Val Glu Ala Leu Tyr Leu Val
1               5                   10                  15

Cys Gly Glu Arg Gly Phe Phe Tyr Thr Ala Pro Thr
            20                  25

<210> SEQ ID NO 23
<211> LENGTH: 27
<212> TYPE: PRT
<213> ORGANISM: Artificial Sequence
<220> FEATURE:
<223> OTHER INFORMATION: des (B1 B3) derivative of (AlaB28, ProB29)
      insulin

<400> SEQUENCE: 23

Gln His Leu Cys Gly Ser His Leu Val Glu Ala Leu Tyr Leu Val Cys
1               5                   10                  15

Gly Glu Arg Gly Phe Phe Tyr Thr Ala Pro Thr
            20                  25

<210> SEQ ID NO 24
<211> LENGTH: 31
<212> TYPE: PRT
<213> ORGANISM: Artificial Sequence
<220> FEATURE:
<223> OTHER INFORMATION: des (B1) derivative of GluB28 insulin
<220> FEATURE:

```
<221> NAME/KEY: MISC_FEATURE
<222> LOCATION: (1)..(2)
<223> OTHER INFORMATION: X is Ala Asn, Glu Asn, Val Ala, Val Glu, Glu
      Ala, or Glu Glu

<400> SEQUENCE: 24

Xaa Xaa Val Asn Gln His Leu Cys Gly Ser His Leu Val Glu Ala Leu
1               5                   10                  15

Tyr Leu Val Cys Gly Glu Arg Gly Phe Phe Tyr Thr Glu Lys Thr
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: des (B1, B2) derivative of GluB28 insulin
<220> FEATURE:
<221> NAME/KEY: MISC_FEATURE
<222> LOCATION: (1)..(2)
<223> OTHER INFORMATION: X is Asn Glu, Asn Ala, Ala Gln, Glu Gln, Ala
      Glu, Glu Glu, or Glu Ala

<400> SEQUENCE: 25

Xaa Xaa Asn Gln His Leu Cys Gly Ser His Leu Val Glu Ala Leu Tyr
1               5                   10                  15

Leu Val Cys Gly Glu Arg Gly Phe Phe Tyr Thr Glu Lys Thr
            20                  25                  30

<210> SEQ ID NO 26
<211> LENGTH: 28
<212> TYPE: PRT
<213> ORGANISM: Artificial Sequence
<220> FEATURE:
<223> OTHER INFORMATION: des (B1 B3) derivative of GluB28 insulin
<220> FEATURE:
<221> NAME/KEY: MISC_FEATURE
<222> LOCATION: (1)..(1)
<223> OTHER INFORMATION: X is Ala or Glu

<400> SEQUENCE: 26

Xaa Gln His Leu Cys Gly Ser His Leu Val Glu Ala Leu Tyr Leu Val
1               5                   10                  15

Cys Gly Glu Arg Gly Phe Phe Tyr Thr Glu Lys Thr
            20                  25

<210> SEQ ID NO 27
<211> LENGTH: 31
<212> TYPE: PRT
<213> ORGANISM: Artificial Sequence
<220> FEATURE:
<223> OTHER INFORMATION: des (B1) derivative of AspB28 insulin
<220> FEATURE:
<221> NAME/KEY: MISC_FEATURE
<222> LOCATION: (1)..(2)
<223> OTHER INFORMATION: X is Ala Asn, Glu Asn, Val Ala, Val Glu, Glu
      Ala, or Glu Glu

<400> SEQUENCE: 27

Xaa Xaa Val Asn Gln His Leu Cys Gly Ser His Leu Val Glu Ala Leu
1               5                   10                  15

Tyr Leu Val Cys Gly Glu Arg Gly Phe Phe Tyr Thr Asp Lys Thr
            20                  25                  30

<210> SEQ ID NO 28
<211> LENGTH: 30
<212> TYPE: PRT
```

```
<213> ORGANISM: Artificial Sequence
<220> FEATURE:
<223> OTHER INFORMATION: des (B1, B2) derivative of AspB28 insulin
<220> FEATURE:
<221> NAME/KEY: MISC_FEATURE
<222> LOCATION: (1)..(2)
<223> OTHER INFORMATION: X is Asn Glu, Asn Ala, Ala Gln, Glu Gln, Ala
      Glu, Glu Glu, or Glu Ala

<400> SEQUENCE: 28

Xaa Xaa Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 29
<211> LENGTH: 28
<212> TYPE: PRT
<213> ORGANISM: Artificial Sequence
<220> FEATURE:
<223> OTHER INFORMATION: des (B1 B3) derivative of AspB28 insulin
<220> FEATURE:
<221> NAME/KEY: MISC_FEATURE
<222> LOCATION: (1)..(1)
<223> OTHER INFORMATION: X is Ala or Glu

<400> SEQUENCE: 29

Xaa Gln His Leu Cys Gly Ser His Leu Val Glu Ala Leu Tyr Leu Val
1               5                   10                  15

Cys Gly Glu Arg Gly Phe Phe Tyr Thr Asp Lys Thr
            20                  25

<210> SEQ ID NO 30
<211> LENGTH: 31
<212> TYPE: PRT
<213> ORGANISM: Artificial Sequence
<220> FEATURE:
<223> OTHER INFORMATION: des (B1) derivative of (LysB28, ProB29) insulin
<220> FEATURE:
<221> NAME/KEY: MISC_FEATURE
<222> LOCATION: (1)..(2)
<223> OTHER INFORMATION: X is Ala Asn, Glu Asn, Val Ala, Val Glu, Glu
      Ala, or Glu Glu

<400> SEQUENCE: 30

Xaa Xaa Val Asn Gln His Leu Cys Gly Ser His Leu Val Glu Ala Leu
1               5                   10                  15

Tyr Leu Val Cys Gly Glu Arg Gly Phe Phe Tyr Thr Lys Pro Thr
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: des (B1, B2) derivative of (LysB28, ProB29)
      insulin
<220> FEATURE:
<221> NAME/KEY: MISC_FEATURE
<222> LOCATION: (1)..(2)
<223> OTHER INFORMATION: X is Asn Glu, Asn Ala, Ala Gln, Glu Gln, Ala
      Glu, Glu Glu, or Glu Ala

<400> SEQUENCE: 31

Xaa Xaa Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 32
<211> LENGTH: 28
<212> TYPE: PRT
<213> ORGANISM: Artificial Sequence
<220> FEATURE:
<223> OTHER INFORMATION: des (B1 B3) derivative of (LysB28, ProB29) insulin
<220> FEATURE:
<221> NAME/KEY: MISC_FEATURE
<222> LOCATION: (1)..(1)
<223> OTHER INFORMATION: X is Ala or Glu

<400> SEQUENCE: 32

Xaa Gln His Leu Cys Gly Ser His Leu Val Glu Ala Leu Tyr Leu Val
1               5                   10                  15

Cys Gly Glu Arg Gly Phe Phe Tyr Thr Lys Pro Thr
            20                  25

<210> SEQ ID NO 33
<211> LENGTH: 31
<212> TYPE: PRT
<213> ORGANISM: Artificial Sequence
<220> FEATURE:
<223> OTHER INFORMATION: des (B1) derivative of (GluB28) insulin
<220> FEATURE:
<221> NAME/KEY: MISC_FEATURE
<222> LOCATION: (1)..(2)
<223> OTHER INFORMATION: X is Ala Asn, Glu Asn, Val Ala, Val Glu, Glu Ala, or Glu Glu

<400> SEQUENCE: 33

Xaa Xaa Val Asn Gln His Leu Cys Gly Ser His Leu Val Glu Ala Leu
1               5                   10                  15

Tyr Leu Val Cys Gly Glu Arg Gly Phe Phe Tyr Thr Glu Lys Thr
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: des (B1, B2) derivative of (AlaB28) insulin
<220> FEATURE:
<221> NAME/KEY: MISC_FEATURE
<222> LOCATION: (1)..(2)
<223> OTHER INFORMATION: X is Asn Glu, Asn Ala, Ala Gln, Glu Gln, Ala Glu, Glu Glu, or Glu Ala

<400> SEQUENCE: 34

Xaa Xaa Asn Gln His Leu Cys Gly Ser His Leu Val Glu Ala Leu Tyr
1               5                   10                  15

Leu Val Cys Gly Glu Arg Gly Phe Phe Tyr Thr Ala Lys Thr
            20                  25                  30

<210> SEQ ID NO 35
<211> LENGTH: 28
<212> TYPE: PRT
<213> ORGANISM: Artificial Sequence
<220> FEATURE:
<223> OTHER INFORMATION: des (B1 B3) derivative of (AlaB28) insulin
<220> FEATURE:
<221> NAME/KEY: MISC_FEATURE
<222> LOCATION: (1)..(1)
<223> OTHER INFORMATION: X is Ala or Glu

<400> SEQUENCE: 35

Xaa Gln His Leu Cys Gly Ser His Leu Val Glu Ala Leu Tyr Leu Val

```
                1               5                   10                  15

Cys Gly Glu Arg Gly Phe Phe Tyr Thr Ala Lys Thr
                20                  25

<210> SEQ ID NO 36
<211> LENGTH: 31
<212> TYPE: PRT
<213> ORGANISM: Artificial Sequence
<220> FEATURE:
<223> OTHER INFORMATION: des (B1) derivative of (GluB28, ProB29) insulin
<220> FEATURE:
<221> NAME/KEY: MISC_FEATURE
<222> LOCATION: (1)..(2)
<223> OTHER INFORMATION: X is Ala Asn, Glu Asn, Val Ala, Val Glu, Glu
      Ala, or Glu Glu

<400> SEQUENCE: 36

Xaa Xaa Val Asn Gln His Leu Cys Gly Ser His Leu Val Glu Ala Leu
1               5                   10                  15

Tyr Leu Val Cys Gly Glu Arg Gly Phe Phe Tyr Thr Glu Pro Thr
                20                  25                  30

<210> SEQ ID NO 37
<211> LENGTH: 30
<212> TYPE: PRT
<213> ORGANISM: Artificial Sequence
<220> FEATURE:
<223> OTHER INFORMATION: des (B1, B2) derivative of (GluB28, ProB29)
      insulin
<220> FEATURE:
<221> NAME/KEY: MISC_FEATURE
<222> LOCATION: (1)..(2)
<223> OTHER INFORMATION: X is Asn Glu, Asn Ala, Ala Gln, Glu Gln, Ala
      Glu, Glu Glu, or Glu Ala

<400> SEQUENCE: 37

Xaa Xaa Asn Gln His Leu Cys Gly Ser His Leu Val Glu Ala Leu Tyr
1               5                   10                  15

Leu Val Cys Gly Glu Arg Gly Phe Phe Tyr Thr Glu Pro Thr
        20                  25                  30

<210> SEQ ID NO 38
<211> LENGTH: 28
<212> TYPE: PRT
<213> ORGANISM: Artificial Sequence
<220> FEATURE:
<223> OTHER INFORMATION: des (B1 B3) derivative of (GluB28, ProB29)
      insulin
<220> FEATURE:
<221> NAME/KEY: MISC_FEATURE
<222> LOCATION: (1)..(1)
<223> OTHER INFORMATION: X is Ala or Glu

<400> SEQUENCE: 38

Xaa Gln His Leu Cys Gly Ser His Leu Val Glu Ala Leu Tyr Leu Val
1               5                   10                  15

Cys Gly Glu Arg Gly Phe Phe Tyr Thr Glu Pro Thr
                20                  25

<210> SEQ ID NO 39
<211> LENGTH: 31
<212> TYPE: PRT
<213> ORGANISM: Artificial Sequence
<220> FEATURE:
<223> OTHER INFORMATION: des (B1) derivative of (AlaB28, ProB29) insulin
<220> FEATURE:
<221> NAME/KEY: MISC_FEATURE
<222> LOCATION: (1)..(2)
```

```
<223> OTHER INFORMATION: X is Ala Asn, Glu Asn, Val Ala, Val Glu, Glu
      Ala, or Glu Glu

<400> SEQUENCE: 39

Xaa Xaa Val Asn Gln His Leu Cys Gly Ser His Leu Val Glu Ala Leu
1               5                   10                  15

Tyr Leu Val Cys Gly Glu Arg Gly Phe Phe Tyr Thr Ala Pro Thr
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: des (B1, B2) derivative of (AlaB28, ProB29)
      insulin
<220> FEATURE:
<221> NAME/KEY: MISC_FEATURE
<222> LOCATION: (1)..(2)
<223> OTHER INFORMATION: X is Asn Glu, Asn Ala, Ala Gln, Glu Gln, Ala
      Glu, Glu Glu, or Glu Ala

<400> SEQUENCE: 40

Xaa Xaa Asn Gln His Leu Cys Gly Ser His Leu Val Glu Ala Leu Tyr
1               5                   10                  15

Leu Val Cys Gly Glu Arg Gly Phe Phe Tyr Thr Ala Pro Thr
            20                  25                  30

<210> SEQ ID NO 41
<211> LENGTH: 28
<212> TYPE: PRT
<213> ORGANISM: Artificial Sequence
<220> FEATURE:
<223> OTHER INFORMATION: des (B1 B3) derivative of (AlaB28, ProB29)
      insulin
<220> FEATURE:
<221> NAME/KEY: MISC_FEATURE
<222> LOCATION: (1)..(1)
<223> OTHER INFORMATION: X is Ala or Glu

<400> SEQUENCE: 41

Xaa Gln His Leu Cys Gly Ser His Leu Val Glu Ala Leu Tyr Leu Val
1               5                   10                  15

Cys Gly Glu Arg Gly Phe Phe Tyr Thr Ala Pro Thr
            20                  25

<210> SEQ ID NO 42
<211> LENGTH: 21
<212> TYPE: PRT
<213> ORGANISM: Artificial Sequence
<220> FEATURE:
<223> OTHER INFORMATION: HA8 EA14 QA17 insulin A-chain

<400> SEQUENCE: 42

Gly Ile Val Glu Gln Cys Cys His Ser Ile Cys Ser Leu Glu Gln Leu
1               5                   10                  15

Gln Asn Tyr Cys Asn
            20

<210> SEQ ID NO 43
<211> LENGTH: 29
<212> TYPE: PRT
<213> ORGANISM: Artificial Sequence
<220> FEATURE:
<223> OTHER INFORMATION: des B1 AB2 EB29 insulin B-chain

<400> SEQUENCE: 43
```

Ala Asn Gln His Leu Cys Gly Ser His Leu Val Glu Ala Leu Tyr Leu
1               5                   10                  15

Val Cys Gly Glu Arg Gly Phe Phe Tyr Thr Pro Glu Thr
            20                  25

<210> SEQ ID NO 44
<211> LENGTH: 21
<212> TYPE: PRT
<213> ORGANISM: Artificial Sequence
<220> FEATURE:
<223> OTHER INFORMATION: EA8 EA14 QA17 insulin A-chain

<400> SEQUENCE: 44

Gly Ile Val Glu Gln Cys Cys Glu Ser Ile Cys Ser Leu Glu Gln Leu
1               5                   10                  15

Gln Asn Tyr Cys Asn
            20

<210> SEQ ID NO 45
<211> LENGTH: 28
<212> TYPE: PRT
<213> ORGANISM: Artificial Sequence
<220> FEATURE:
<223> OTHER INFORMATION: des B1 AB2 des B30 insulin B-chain

<400> SEQUENCE: 45

Ala Asn Gln His Leu Cys Gly Ser His Leu Val Glu Ala Leu Tyr Leu
1               5                   10                  15

Val Cys Gly Glu Arg Gly Phe Phe Tyr Thr Pro Lys
            20                  25

<210> SEQ ID NO 46
<211> LENGTH: 28
<212> TYPE: PRT
<213> ORGANISM: Artificial Sequence
<220> FEATURE:
<223> OTHER INFORMATION: des B1 EB2 des B30 insulin B-chain

<400> SEQUENCE: 46

Glu Asn Gln His Leu Cys Gly Ser His Leu Val Glu Ala Leu Tyr Leu
1               5                   10                  15

Val Cys Gly Glu Arg Gly Phe Phe Tyr Thr Pro Lys
            20                  25

<210> SEQ ID NO 47
<211> LENGTH: 27
<212> TYPE: PRT
<213> ORGANISM: Artificial Sequence
<220> FEATURE:
<223> OTHER INFORMATION: des [B1 B2] EB3 des B30 insulin B-chain

<400> SEQUENCE: 47

Glu Gln His Leu Cys Gly Ser His Leu Val Glu Ala Leu Tyr Leu Val
1               5                   10                  15

Cys Gly Glu Arg Gly Phe Phe Tyr Thr Pro Lys
            20                  25

<210> SEQ ID NO 48
<211> LENGTH: 28
<212> TYPE: PRT
<213> ORGANISM: Artificial Sequence
<220> FEATURE:
<223> OTHER INFORMATION: des B1 des B30 insulin B-chain

```
<400> SEQUENCE: 48

Val Asn Gln His Leu Cys Gly Ser His Leu Val Glu Ala Leu Tyr Leu
1               5                   10                  15

Val Cys Gly Glu Arg Gly Phe Phe Tyr Thr Pro Lys
            20                  25

<210> SEQ ID NO 49
<211> LENGTH: 21
<212> TYPE: PRT
<213> ORGANISM: Artificial Sequence
<220> FEATURE:
<223> OTHER INFORMATION: HA8, EA14 insulin A-chain

<400> SEQUENCE: 49

Gly Ile Val Glu Gln Cys Cys Glu Ser Ile Cys Ser Leu Glu Gln Leu
1               5                   10                  15

Arg Asn Tyr Cys Asn
            20

<210> SEQ ID NO 50
<211> LENGTH: 29
<212> TYPE: PRT
<213> ORGANISM: Artificial Sequence
<220> FEATURE:
<223> OTHER INFORMATION: des B1, EB29 insulin B-chain

<400> SEQUENCE: 50

Val Asn Gln His Leu Cys Gly Ser His Leu Val Glu Ala Leu Tyr Leu
1               5                   10                  15

Val Cys Gly Glu Arg Gly Phe Phe Tyr Thr Pro Glu Thr
            20                  25

<210> SEQ ID NO 51
<211> LENGTH: 28
<212> TYPE: PRT
<213> ORGANISM: Artificial Sequence
<220> FEATURE:
<223> OTHER INFORMATION: desB1 QB13 desB30 insulin B-chain

<400> SEQUENCE: 51

Val Asn Gln His Leu Cys Gly Ser His Leu Val Gln Ala Leu Tyr Leu
1               5                   10                  15

Val Cys Gly Glu Arg Gly Phe Phe Tyr Thr Pro Lys
            20                  25

<210> SEQ ID NO 52
<211> LENGTH: 21
<212> TYPE: PRT
<213> ORGANISM: Artificial Sequence
<220> FEATURE:
<223> OTHER INFORMATION: EA8, EA14 RA17 insulin A-chain

<400> SEQUENCE: 52

Gly Ile Val Glu Gln Cys Cys Glu Ser Ile Cys Ser Leu Glu Gln Leu
1               5                   10                  15

Arg Asn Tyr Cys Asn
            20

<210> SEQ ID NO 53
<211> LENGTH: 28
<212> TYPE: PRT
<213> ORGANISM: Artificial Sequence
<220> FEATURE:
<223> OTHER INFORMATION: desB1 QB13 EB 22 desB30 insulin B-chain
```

```
<400> SEQUENCE: 53

Val Asn Gln His Leu Cys Gly Ser His Leu Val Gln Ala Leu Tyr Leu
1               5                   10                  15

Val Cys Gly Glu Glu Gly Phe Phe Tyr Thr Pro Lys
            20                  25

<210> SEQ ID NO 54
<211> LENGTH: 21
<212> TYPE: PRT
<213> ORGANISM: Artificial Sequence
<220> FEATURE:
<223> OTHER INFORMATION: HA8 EA14 RA17 insulin A-chain

<400> SEQUENCE: 54

Gly Ile Val Glu Gln Cys Cys His Ser Ile Cys Ser Leu Glu Gln Leu
1               5                   10                  15

Arg Asn Tyr Cys Asn
            20

<210> SEQ ID NO 55
<211> LENGTH: 28
<212> TYPE: PRT
<213> ORGANISM: Artificial Sequence
<220> FEATURE:
<223> OTHER INFORMATION: des B1 EB 22 des B30 insulin B-chain

<400> SEQUENCE: 55

Val Asn Gln His Leu Cys Gly Ser His Leu Val Glu Ala Leu Tyr Leu
1               5                   10                  15

Val Cys Gly Glu Glu Gly Phe Phe Tyr Thr Pro Lys
            20                  25

<210> SEQ ID NO 56
<211> LENGTH: 29
<212> TYPE: PRT
<213> ORGANISM: Artificial Sequence
<220> FEATURE:
<223> OTHER INFORMATION: des B1, QB13 EB29 insulin B-chain

<400> SEQUENCE: 56

Val Asn Gln His Leu Cys Gly Ser His Leu Val Gln Ala Leu Tyr Leu
1               5                   10                  15

Val Cys Gly Glu Arg Gly Phe Phe Tyr Thr Pro Glu Thr
            20                  25

<210> SEQ ID NO 57
<211> LENGTH: 21
<212> TYPE: PRT
<213> ORGANISM: Artificial Sequence
<220> FEATURE:
<223> OTHER INFORMATION: HA8 WA13 insulin A-chain

<400> SEQUENCE: 57

Gly Ile Val Glu Gln Cys Cys His Ser Ile Cys Ser Trp Tyr Gln Leu
1               5                   10                  15

Glu Asn Tyr Cys Asn
            20

<210> SEQ ID NO 58
<211> LENGTH: 21
<212> TYPE: PRT
<213> ORGANISM: Artificial Sequence
<220> FEATURE:
```

<223> OTHER INFORMATION: HA8 LA14 QA17 insulin A-chain

<400> SEQUENCE: 58

Gly Ile Val Glu Gln Cys Cys His Ser Ile Cys Ser Leu Leu Gln Leu
1               5                   10                  15

Gln Asn Tyr Cys Asn
            20

<210> SEQ ID NO 59
<211> LENGTH: 21
<212> TYPE: PRT
<213> ORGANISM: Artificial Sequence
<220> FEATURE:
<223> OTHER INFORMATION: EA8 WA13 insulin A-chain

<400> SEQUENCE: 59

Gly Ile Val Glu Gln Cys Cys Glu Ser Ile Cys Ser Trp Tyr Gln Leu
1               5                   10                  15

Glu Asn Tyr Cys Asn
            20

<210> SEQ ID NO 60
<211> LENGTH: 21
<212> TYPE: PRT
<213> ORGANISM: Artificial Sequence
<220> FEATURE:
<223> OTHER INFORMATION: EA8 insulin A-chain

<400> SEQUENCE: 60

Gly Ile Val Glu Gln Cys Cys Glu Ser Ile Cys Ser Leu Tyr Gln Leu
1               5                   10                  15

Glu Asn Tyr Cys Asn
            20

<210> SEQ ID NO 61
<211> LENGTH: 21
<212> TYPE: PRT
<213> ORGANISM: Artificial Sequence
<220> FEATURE:
<223> OTHER INFORMATION: EA8 LA14 RA17 insulin A-chain

<400> SEQUENCE: 61

Gly Ile Val Glu Gln Cys Cys Glu Ser Ile Cys Ser Leu Leu Gln Leu
1               5                   10                  15

Arg Asn Tyr Cys Asn
            20

<210> SEQ ID NO 62
<211> LENGTH: 29
<212> TYPE: PRT
<213> ORGANISM: Artificial Sequence
<220> FEATURE:
<223> OTHER INFORMATION: des B1 EB2 EB29 insulin B-chain

<400> SEQUENCE: 62

Glu Asn Gln His Leu Cys Gly Ser His Leu Val Glu Ala Leu Tyr Leu
1               5                   10                  15

Val Cys Gly Glu Arg Gly Phe Phe Tyr Thr Pro Glu Thr
            20                  25

<210> SEQ ID NO 63
<211> LENGTH: 28
<212> TYPE: PRT
<213> ORGANISM: Artificial Sequence
<220> FEATURE:
<223> OTHER INFORMATION: des B1 EB2 EB17 des B30 insulin B-chain

<400> SEQUENCE: 63

Glu Asn Gln His Leu Cys Gly Ser His Leu Val Glu Ala Leu Tyr Glu
1               5                   10                  15

Val Cys Gly Glu Arg Gly Phe Phe Tyr Thr Pro Lys
            20                  25

<210> SEQ ID NO 64
<211> LENGTH: 28
<212> TYPE: PRT
<213> ORGANISM: Artificial Sequence
<220> FEATURE:
<223> OTHER INFORMATION: des B1 EB2 FB17 des B30 insulin B-chain

<400> SEQUENCE: 64

Glu Asn Gln His Leu Cys Gly Ser His Leu Val Glu Ala Leu Tyr Phe
1               5                   10                  15

Val Cys Gly Glu Arg Gly Phe Phe Tyr Thr Pro Lys
            20                  25

<210> SEQ ID NO 65
<211> LENGTH: 28
<212> TYPE: PRT
<213> ORGANISM: Artificial Sequence
<220> FEATURE:
<223> OTHER INFORMATION: des B1 EB2 NB17 des B30 insulin B-chain

<400> SEQUENCE: 65

Glu Asn Gln His Leu Cys Gly Ser His Leu Val Glu Ala Leu Tyr Asn
1               5                   10                  15

Val Cys Gly Glu Arg Gly Phe Phe Tyr Thr Pro Lys
            20                  25

<210> SEQ ID NO 66
<211> LENGTH: 28
<212> TYPE: PRT
<213> ORGANISM: Artificial Sequence
<220> FEATURE:
<223> OTHER INFORMATION: des B1 AB2 EB17 des B30 insulin B-chain

<400> SEQUENCE: 66

Ala Asn Gln His Leu Cys Gly Ser His Leu Val Glu Ala Leu Tyr Glu
1               5                   10                  15

Val Cys Gly Glu Arg Gly Phe Phe Tyr Thr Pro Lys
            20                  25

<210> SEQ ID NO 67
<211> LENGTH: 28
<212> TYPE: PRT
<213> ORGANISM: Artificial Sequence
<220> FEATURE:
<223> OTHER INFORMATION: des B1 AB2 FB17 des B30 insulin B-chain

<400> SEQUENCE: 67

Ala Asn Gln His Leu Cys Gly Ser His Leu Val Glu Ala Leu Tyr Phe
1               5                   10                  15

Val Cys Gly Glu Arg Gly Phe Phe Tyr Thr Pro Lys
            20                  25

<210> SEQ ID NO 68
<211> LENGTH: 28
<212> TYPE: PRT

```
<213> ORGANISM: Artificial Sequence
<220> FEATURE:
<223> OTHER INFORMATION: des [B1, B2] EB29 insulin B-chain

<400> SEQUENCE: 68

Asn Gln His Leu Cys Gly Ser His Leu Val Glu Ala Leu Tyr Leu Val
1               5                   10                  15

Cys Gly Glu Arg Gly Phe Phe Tyr Thr Pro Glu Thr
            20                  25

<210> SEQ ID NO 69
<211> LENGTH: 27
<212> TYPE: PRT
<213> ORGANISM: Artificial Sequence
<220> FEATURE:
<223> OTHER INFORMATION: des [B1, B2] des B30 insulin B-chain

<400> SEQUENCE: 69

Asn Gln His Leu Cys Gly Ser His Leu Val Glu Ala Leu Tyr Leu Val
1               5                   10                  15

Cys Gly Glu Arg Gly Phe Phe Tyr Thr Pro Lys
            20                  25

<210> SEQ ID NO 70
<211> LENGTH: 27
<212> TYPE: PRT
<213> ORGANISM: Artificial Sequence
<220> FEATURE:
<223> OTHER INFORMATION: des [B1, B2] QB13 des B30 insulin B-chain

<400> SEQUENCE: 70

Asn Gln His Leu Cys Gly Ser His Leu Val Gln Ala Leu Tyr Leu Val
1               5                   10                  15

Cys Gly Glu Arg Gly Phe Phe Tyr Thr Pro Lys
            20                  25

<210> SEQ ID NO 71
<211> LENGTH: 28
<212> TYPE: PRT
<213> ORGANISM: Artificial Sequence
<220> FEATURE:
<223> OTHER INFORMATION: des [B1, B2] QB13, EB29 insulin B-chain

<400> SEQUENCE: 71

Asn Gln His Leu Cys Gly Ser His Leu Val Gln Ala Leu Tyr Leu Val
1               5                   10                  15

Cys Gly Glu Arg Gly Phe Phe Tyr Thr Pro Glu Thr
            20                  25

<210> SEQ ID NO 72
<211> LENGTH: 27
<212> TYPE: PRT
<213> ORGANISM: Artificial Sequence
<220> FEATURE:
<223> OTHER INFORMATION: des [B1, B2] QB13 EB22 des B30 insulin B-chain

<400> SEQUENCE: 72

Asn Gln His Leu Cys Gly Ser His Leu Val Gln Ala Leu Tyr Leu Val
1               5                   10                  15

Cys Gly Glu Glu Gly Phe Phe Tyr Thr Pro Lys
            20                  25

<210> SEQ ID NO 73
<211> LENGTH: 27
```

```
<212> TYPE: PRT
<213> ORGANISM: Artificial Sequence
<220> FEATURE:
<223> OTHER INFORMATION: des [B1, B2] EB 22 des B30 insulin B-chain

<400> SEQUENCE: 73

Asn Gln His Leu Cys Gly Ser His Leu Val Glu Ala Leu Tyr Leu Val
1               5                   10                  15

Cys Gly Glu Glu Gly Phe Phe Tyr Thr Pro Lys
            20                  25

<210> SEQ ID NO 74
<211> LENGTH: 21
<212> TYPE: PRT
<213> ORGANISM: Artificial Sequence
<220> FEATURE:
<223> OTHER INFORMATION: EA8 LA14 QA17 insulin A-chain

<400> SEQUENCE: 74

Gly Ile Val Glu Gln Cys Cys Glu Ser Ile Cys Ser Leu Leu Gln Leu
1               5                   10                  15

Gln Asn Tyr Cys Asn
            20

<210> SEQ ID NO 75
<211> LENGTH: 21
<212> TYPE: PRT
<213> ORGANISM: Artificial Sequence
<220> FEATURE:
<223> OTHER INFORMATION: HA8 insulin A-chain

<400> SEQUENCE: 75

Gly Ile Val Glu Gln Cys Cys His Ser Ile Cys Ser Leu Tyr Gln Leu
1               5                   10                  15

Glu Asn Tyr Cys Asn
            20

<210> SEQ ID NO 76
<211> LENGTH: 21
<212> TYPE: PRT
<213> ORGANISM: Artificial Sequence
<220> FEATURE:
<223> OTHER INFORMATION: EA8 LA14 insulin A-chain

<400> SEQUENCE: 76

Gly Ile Val Glu Gln Cys Cys Glu Ser Ile Cys Ser Leu Leu Gln Leu
1               5                   10                  15

Glu Asn Tyr Cys Asn
            20

<210> SEQ ID NO 77
<211> LENGTH: 21
<212> TYPE: PRT
<213> ORGANISM: Artificial Sequence
<220> FEATURE:
<223> OTHER INFORMATION: EA8 EA14 insulin A-chain

<400> SEQUENCE: 77

Gly Ile Val Glu Gln Cys Cys Glu Ser Ile Cys Ser Leu Glu Gln Leu
1               5                   10                  15

Glu Asn Tyr Cys Asn
            20

<210> SEQ ID NO 78
```

```
<211> LENGTH: 21
<212> TYPE: PRT
<213> ORGANISM: Artificial Sequence
<220> FEATURE:
<223> OTHER INFORMATION: EA8 QA17 insulin A-chain

<400> SEQUENCE: 78

Gly Ile Val Glu Gln Cys Cys Glu Ser Ile Cys Ser Leu Tyr Gln Leu
1               5                   10                  15

Gln Asn Tyr Cys Asn
            20

<210> SEQ ID NO 79
<211> LENGTH: 21
<212> TYPE: PRT
<213> ORGANISM: Artificial Sequence
<220> FEATURE:
<223> OTHER INFORMATION: EA8 WA13 EA14 insulin A-chain

<400> SEQUENCE: 79

Gly Ile Val Glu Gln Cys Cys Glu Ser Ile Cys Ser Trp Glu Gln Leu
1               5                   10                  15

Glu Asn Tyr Cys Asn
            20

<210> SEQ ID NO 80
<211> LENGTH: 21
<212> TYPE: PRT
<213> ORGANISM: Artificial Sequence
<220> FEATURE:
<223> OTHER INFORMATION: HA8 WA13 EA14 insulin A-chain

<400> SEQUENCE: 80

Gly Ile Val Glu Gln Cys Cys His Ser Ile Cys Ser Trp Glu Gln Leu
1               5                   10                  15

Glu Asn Tyr Cys Asn
            20

<210> SEQ ID NO 81
<211> LENGTH: 27
<212> TYPE: PRT
<213> ORGANISM: Artificial Sequence
<220> FEATURE:
<223> OTHER INFORMATION: des [B1, B2] AB3 des B30 insulin B-chain

<400> SEQUENCE: 81

Ala Gln His Leu Cys Gly Ser His Leu Val Glu Ala Leu Tyr Leu Val
1               5                   10                  15

Cys Gly Glu Arg Gly Phe Phe Tyr Thr Pro Lys
            20                  25

<210> SEQ ID NO 82
<211> LENGTH: 27
<212> TYPE: PRT
<213> ORGANISM: Artificial Sequence
<220> FEATURE:
<223> OTHER INFORMATION: des [B1, B2] EB3 des B30 insulin B-chain

<400> SEQUENCE: 82

Glu Gln His Leu Cys Gly Ser His Leu Val Glu Ala Leu Tyr Leu Val
1               5                   10                  15

Cys Gly Glu Arg Gly Phe Phe Tyr Thr Pro Lys
            20                  25
```

```
<210> SEQ ID NO 83
<211> LENGTH: 28
<212> TYPE: PRT
<213> ORGANISM: Artificial Sequence
<220> FEATURE:
<223> OTHER INFORMATION: des [B1,B2] EB3 EB29 insulin B-chain

<400> SEQUENCE: 83

Glu Gln His Leu Cys Gly Ser His Leu Val Glu Ala Leu Tyr Leu Val
1               5                   10                  15

Cys Gly Glu Arg Gly Phe Phe Tyr Thr Pro Glu Thr
            20                  25

<210> SEQ ID NO 84
<211> LENGTH: 28
<212> TYPE: PRT
<213> ORGANISM: Artificial Sequence
<220> FEATURE:
<223> OTHER INFORMATION: des [B1,B2] AB3 EB29 insulin B-chain

<400> SEQUENCE: 84

Ala Gln His Leu Cys Gly Ser His Leu Val Glu Ala Leu Tyr Leu Val
1               5                   10                  15

Cys Gly Glu Arg Gly Phe Phe Tyr Thr Pro Glu Thr
            20                  25

<210> SEQ ID NO 85
<211> LENGTH: 27
<212> TYPE: PRT
<213> ORGANISM: Artificial Sequence
<220> FEATURE:
<223> OTHER INFORMATION: des [B1, B2] EB3 FB17 des B30 insulin B-chain

<400> SEQUENCE: 85

Glu Gln His Leu Cys Gly Ser His Leu Val Glu Ala Leu Tyr Phe Val
1               5                   10                  15

Cys Gly Glu Arg Gly Phe Phe Tyr Thr Pro Lys
            20                  25

<210> SEQ ID NO 86
<211> LENGTH: 27
<212> TYPE: PRT
<213> ORGANISM: Artificial Sequence
<220> FEATURE:
<223> OTHER INFORMATION: des [B1, B2] EB3 EB17 des B30 insulin B-chain

<400> SEQUENCE: 86

Glu Gln His Leu Cys Gly Ser His Leu Val Glu Ala Leu Tyr Glu Val
1               5                   10                  15

Cys Gly Glu Arg Gly Phe Phe Tyr Thr Pro Lys
            20                  25

<210> SEQ ID NO 87
<211> LENGTH: 27
<212> TYPE: PRT
<213> ORGANISM: Artificial Sequence
<220> FEATURE:
<223> OTHER INFORMATION: des [B1, B2] EB3 NB17 des B30 insulin B-chain

<400> SEQUENCE: 87

Glu Gln His Leu Cys Gly Ser His Leu Val Glu Ala Leu Tyr Asn Val
1               5                   10                  15

Cys Gly Glu Arg Gly Phe Phe Tyr Thr Pro Lys
            20                  25
```

<210> SEQ ID NO 88
<211> LENGTH: 28
<212> TYPE: PRT
<213> ORGANISM: Artificial Sequence
<220> FEATURE:
<223> OTHER INFORMATION: des [B1,B2] EB3 FB17 EB29 insulin B-chain

<400> SEQUENCE: 88

Glu Gln His Leu Cys Gly Ser His Leu Val Glu Ala Leu Tyr Phe Val
1               5                   10                  15

Cys Gly Glu Arg Gly Phe Phe Tyr Thr Pro Glu Thr
            20                  25

<210> SEQ ID NO 89
<211> LENGTH: 26
<212> TYPE: PRT
<213> ORGANISM: Artificial Sequence
<220> FEATURE:
<223> OTHER INFORMATION: des [B1-B3] des B30 insulin B-chain

<400> SEQUENCE: 89

Gln His Leu Cys Gly Ser His Leu Val Glu Ala Leu Tyr Leu Val Cys
1               5                   10                  15

Gly Glu Arg Gly Phe Phe Tyr Thr Pro Lys
            20                  25

<210> SEQ ID NO 90
<211> LENGTH: 26
<212> TYPE: PRT
<213> ORGANISM: Artificial Sequence
<220> FEATURE:
<223> OTHER INFORMATION: des [B1-B3] QB13 des B30 insulin B-chain

<400> SEQUENCE: 90

Gln His Leu Cys Gly Ser His Leu Val Gln Ala Leu Tyr Leu Val Cys
1               5                   10                  15

Gly Glu Arg Gly Phe Phe Tyr Thr Pro Lys
            20                  25

<210> SEQ ID NO 91
<211> LENGTH: 27
<212> TYPE: PRT
<213> ORGANISM: Artificial Sequence
<220> FEATURE:
<223> OTHER INFORMATION: des [B1-B3] EB29 insulin B-chain

<400> SEQUENCE: 91

Gln His Leu Cys Gly Ser His Leu Val Glu Ala Leu Tyr Leu Val Cys
1               5                   10                  15

Gly Glu Arg Gly Phe Phe Tyr Thr Pro Glu Thr
            20                  25

<210> SEQ ID NO 92
<211> LENGTH: 27
<212> TYPE: PRT
<213> ORGANISM: Artificial Sequence
<220> FEATURE:
<223> OTHER INFORMATION: des [B1-B3] QB13 EB29 insulin B-chain

<400> SEQUENCE: 92

Gln His Leu Cys Gly Ser His Leu Val Gln Ala Leu Tyr Leu Val Cys
1               5                   10                  15

Gly Glu Arg Gly Phe Phe Tyr Thr Pro Glu Thr
            20                  25

<210> SEQ ID NO 93
<211> LENGTH: 26
<212> TYPE: PRT
<213> ORGANISM: Artificial Sequence
<220> FEATURE:
<223> OTHER INFORMATION: des [B1-B3] QB13 EB22 des B30 insulin B-chain

<400> SEQUENCE: 93

Gln His Leu Cys Gly Ser His Leu Val Gln Ala Leu Tyr Leu Val Cys
1               5                   10                  15

Gly Glu Glu Gly Phe Phe Tyr Thr Pro Lys
            20                  25

<210> SEQ ID NO 94
<211> LENGTH: 26
<212> TYPE: PRT
<213> ORGANISM: Artificial Sequence
<220> FEATURE:
<223> OTHER INFORMATION: des [B1-B3] QB13 FB17 des B30 insulin B-chain

<400> SEQUENCE: 94

Gln His Leu Cys Gly Ser His Leu Val Gln Ala Leu Tyr Phe Val Cys
1               5                   10                  15

Gly Glu Arg Gly Phe Phe Tyr Thr Pro Lys
            20                  25

<210> SEQ ID NO 95
<211> LENGTH: 26
<212> TYPE: PRT
<213> ORGANISM: Artificial Sequence
<220> FEATURE:
<223> OTHER INFORMATION: des [B1-B3] FB17 des B30 insulin B-chain

<400> SEQUENCE: 95

Gln His Leu Cys Gly Ser His Leu Val Glu Ala Leu Tyr Phe Val Cys
1               5                   10                  15

Gly Glu Arg Gly Phe Phe Tyr Thr Pro Lys
            20                  25

<210> SEQ ID NO 96
<211> LENGTH: 27
<212> TYPE: PRT
<213> ORGANISM: Artificial Sequence
<220> FEATURE:
<223> OTHER INFORMATION: des [B1-B3] FB17 EB29 insulin B-chain

<400> SEQUENCE: 96

Gln His Leu Cys Gly Ser His Leu Val Glu Ala Leu Tyr Phe Val Cys
1               5                   10                  15

Gly Glu Arg Gly Phe Phe Tyr Thr Pro Glu Thr
            20                  25

<210> SEQ ID NO 97
<211> LENGTH: 27
<212> TYPE: PRT
<213> ORGANISM: Artificial Sequence
<220> FEATURE:
<223> OTHER INFORMATION: des [B1-B3] QB13 FB17 EB29 insulin B-chain

<400> SEQUENCE: 97

Gln His Leu Cys Gly Ser His Leu Val Gln Ala Leu Tyr Phe Val Cys
1               5                   10                  15

Gly Glu Arg Gly Phe Phe Tyr Thr Pro Glu Thr

```
                        20                  25

<210> SEQ ID NO 98
<211> LENGTH: 26
<212> TYPE: PRT
<213> ORGANISM: Artificial Sequence
<220> FEATURE:
<223> OTHER INFORMATION: des [B1-B3] EB4 des B30 insulin B-chain

<400> SEQUENCE: 98

Glu His Leu Cys Gly Ser His Leu Val Glu Ala Leu Tyr Leu Val Cys
1               5                   10                  15

Gly Glu Arg Gly Phe Phe Tyr Thr Pro Lys
            20                  25

<210> SEQ ID NO 99
<211> LENGTH: 26
<212> TYPE: PRT
<213> ORGANISM: Artificial Sequence
<220> FEATURE:
<223> OTHER INFORMATION: des [B1-B3] AB4 des B30 insulin B-chain

<400> SEQUENCE: 99

Ala His Leu Cys Gly Ser His Leu Val Glu Ala Leu Tyr Leu Val Cys
1               5                   10                  15

Gly Glu Arg Gly Phe Phe Tyr Thr Pro Lys
            20                  25

<210> SEQ ID NO 100
<211> LENGTH: 27
<212> TYPE: PRT
<213> ORGANISM: Artificial Sequence
<220> FEATURE:
<223> OTHER INFORMATION: des [B1-B3] EB4 EB29 insulin B-chain

<400> SEQUENCE: 100

Glu His Leu Cys Gly Ser His Leu Val Glu Ala Leu Tyr Leu Val Cys
1               5                   10                  15

Gly Glu Arg Gly Phe Phe Tyr Thr Pro Glu Thr
            20                  25

<210> SEQ ID NO 101
<211> LENGTH: 27
<212> TYPE: PRT
<213> ORGANISM: Artificial Sequence
<220> FEATURE:
<223> OTHER INFORMATION: des [B1-B3] AB4 EB29 insulin B-chain

<400> SEQUENCE: 101

Ala His Leu Cys Gly Ser His Leu Val Glu Ala Leu Tyr Leu Val Cys
1               5                   10                  15

Gly Glu Arg Gly Phe Phe Tyr Thr Pro Glu Thr
            20                  25

<210> SEQ ID NO 102
<211> LENGTH: 26
<212> TYPE: PRT
<213> ORGANISM: Artificial Sequence
<220> FEATURE:
<223> OTHER INFORMATION: des [B1-B3] EB4 FB17 des B30 insulin B-chain

<400> SEQUENCE: 102

Glu His Leu Cys Gly Ser His Leu Val Glu Ala Leu Tyr Phe Val Cys
1               5                   10                  15
```

Gly Glu Arg Gly Phe Phe Tyr Thr Pro Lys
            20                  25

<210> SEQ ID NO 103
<211> LENGTH: 26
<212> TYPE: PRT
<213> ORGANISM: Artificial Sequence
<220> FEATURE:
<223> OTHER INFORMATION: des [B1-B3] EB4 EB17 des B30 insulin B-chain

<400> SEQUENCE: 103

Glu His Leu Cys Gly Ser His Leu Val Glu Ala Leu Tyr Glu Val Cys
1               5                   10                  15

Gly Glu Arg Gly Phe Phe Tyr Thr Pro Lys
            20                  25

<210> SEQ ID NO 104
<211> LENGTH: 29
<212> TYPE: PRT
<213> ORGANISM: Artificial Sequence
<220> FEATURE:
<223> OTHER INFORMATION: des B1 KB2 AB3 EB17 insulin B-chain

<400> SEQUENCE: 104

Lys Ala Gln His Leu Cys Gly Ser His Leu Val Glu Ala Leu Tyr Glu
1               5                   10                  15

Val Cys Gly Glu Arg Gly Phe Phe Tyr Thr Pro Lys Thr
            20                  25

<210> SEQ ID NO 105

<400> SEQUENCE: 105

000

<210> SEQ ID NO 106
<211> LENGTH: 29
<212> TYPE: PRT
<213> ORGANISM: Artificial Sequence
<220> FEATURE:
<223> OTHER INFORMATION: des B1 KB2 EB3 EB17 insulin B-chain

<400> SEQUENCE: 106

Lys Glu Gln His Leu Cys Gly Ser His Leu Val Glu Ala Leu Tyr Glu
1               5                   10                  15

Val Cys Gly Glu Arg Gly Phe Phe Tyr Thr Pro Lys Thr
            20                  25

<210> SEQ ID NO 107
<211> LENGTH: 29
<212> TYPE: PRT
<213> ORGANISM: Artificial Sequence
<220> FEATURE:
<223> OTHER INFORMATION: des B1 KB2 EB3 FB17 insulin B-chain

<400> SEQUENCE: 107

Lys Glu Gln His Leu Cys Gly Ser His Leu Val Glu Ala Leu Tyr Phe
1               5                   10                  15

Val Cys Gly Glu Arg Gly Phe Phe Tyr Thr Pro Lys Thr
            20                  25

<210> SEQ ID NO 108
<211> LENGTH: 30
<212> TYPE: PRT
<213> ORGANISM: Artificial Sequence

```
<220> FEATURE:
<223> OTHER INFORMATION: KB2 AB3 EB17 insulin B-chain

<400> SEQUENCE: 108

Phe Lys Ala Gln His Leu Cys Gly Ser His Leu Val Glu Ala Leu Tyr
1               5                   10                  15

Glu Val Cys Gly Glu Arg Gly Phe Phe Tyr Thr Pro Lys Thr
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: KB2 AB3 FB17 insulin B-chain

<400> SEQUENCE: 109

Phe Lys Ala Gln His Leu Cys Gly Ser His Leu Val Glu Ala Leu Tyr
1               5                   10                  15

Phe Val Cys Gly Glu Arg Gly Phe Phe Tyr Thr Pro Lys Thr
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: KB2 EB3 EB17 insulin B-chain

<400> SEQUENCE: 110

Phe Lys Glu Gln His Leu Cys Gly Ser His Leu Val Glu Ala Leu Tyr
1               5                   10                  15

Glu Val Cys Gly Glu Arg Gly Phe Phe Tyr Thr Pro Lys Thr
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: KB2 EB3 FB17 insulin B-chain

<400> SEQUENCE: 111

Phe Lys Glu Gln His Leu Cys Gly Ser His Leu Val Glu Ala Leu Tyr
1               5                   10                  15

Phe Val Cys Gly Glu Arg Gly Phe Phe Tyr Thr Pro Lys Thr
            20                  25                  30
```